(12) United States Patent
Wolf et al.

(10) Patent No.: US 12,246,009 B2
(45) Date of Patent: Mar. 11, 2025

(54) COMPOSITIONS AND METHODS FOR TREATING NEURODEGENERATIVE, MYODEGENERATIVE, AND LYSOSOMAL STORAGE DISORDERS

(71) Applicant: GEORGETOWN UNIVERSITY, Washington, DC (US)

(72) Inventors: Christian Wolf, Washington, DC (US); Balaraman Kaluvu, Washington, DC (US); Charbel Moussa, Washington, DC (US)

(73) Assignee: Georgetown University, Washington, DC (US)

( * ) Notice: Subject to any disclaimer, the term of this patent is extended or adjusted under 35 U.S.C. 154(b) by 812 days.

(21) Appl. No.: 17/295,553

(22) PCT Filed: Nov. 20, 2019

(86) PCT No.: PCT/US2019/062387
§ 371 (c)(1),
(2) Date: May 20, 2021

(87) PCT Pub. No.: WO2020/106825
PCT Pub. Date: May 28, 2020

(65) Prior Publication Data
US 2021/0369687 A1    Dec. 2, 2021

Related U.S. Application Data

(60) Provisional application No. 62/769,791, filed on Nov. 20, 2018.

(51) Int. Cl.
| | | |
|---|---|---|
| *A61K 31/4365* | (2006.01) | |
| *A61K 31/13* | (2006.01) | |
| *A61K 31/198* | (2006.01) | |
| *A61K 31/27* | (2006.01) | |
| *A61K 31/428* | (2006.01) | |
| *A61K 31/445* | (2006.01) | |
| *A61K 31/4745* | (2006.01) | |
| *A61K 31/519* | (2006.01) | |
| *A61K 35/28* | (2015.01) | |
| *A61K 45/06* | (2006.01) | |
| *A61K 48/00* | (2006.01) | |
| *A61P 25/28* | (2006.01) | |
| *C07D 495/04* | (2006.01) | |

(52) U.S. Cl.
CPC .......... *A61K 31/4365* (2013.01); *A61K 31/13* (2013.01); *A61K 31/198* (2013.01); *A61K 31/27* (2013.01); *A61K 31/428* (2013.01); *A61K 31/445* (2013.01); *A61K 31/4745* (2013.01); *A61K 31/519* (2013.01); *A61K 35/28* (2013.01); *A61K 45/06* (2013.01); *A61P 25/28* (2018.01); *C07D 495/04* (2013.01); *A61K 48/00* (2013.01)

(58) Field of Classification Search
CPC .. A61K 31/4365; A61K 31/13; A61K 31/198; A61K 31/27; A61K 31/428; A61K 31/445; A61K 31/4745; A61K 31/519; A61K 45/06; A61K 35/28; A61K 48/00; A61P 25/28; C07D 495/04
See application file for complete search history.

(56) References Cited

U.S. PATENT DOCUMENTS

| | | |
|---|---|---|
| 6,379,666 B1 | 4/2002 | Tobinick |
| 7,595,306 B2 | 9/2009 | Bumcrot |
| 7,687,512 B2 | 3/2010 | Bilbe |
| 8,232,402 B2 | 7/2012 | Lansbury, Jr. et al. |
| 9,061,029 B2 | 6/2015 | Gallagher et al. |
| 9,474,753 B2 | 10/2016 | Moussa |
| 9,539,259 B2 | 1/2017 | Zack et al. |
| 10,709,704 B2 | 7/2020 | Moussa |
| 2004/0028673 A1 | 2/2004 | Netzer et al. |
| 2004/0038673 A1 | 2/2004 | Dunn et al. |
| 2005/0222091 A1 | 10/2005 | Moussy et al. |
| 2005/0256140 A1 | 11/2005 | Luke et al. |
| 2007/0099941 A1 | 5/2007 | Cai et al. |
| 2007/0197537 A1 | 8/2007 | Blake et al. |
| 2008/0103107 A1 | 5/2008 | Ward et al. |
| 2009/0149485 A1 | 6/2009 | Vituduki Narayana Iyengar et al. |
| 2009/0258814 A1 | 10/2009 | Brady et al. |
| 2012/0083001 A1 | 4/2012 | Suzuki et al. |
| 2012/0083003 A1 | 4/2012 | Johnston et al. |
| 2013/0072482 A1 | 3/2013 | Yang et al. |

(Continued)

FOREIGN PATENT DOCUMENTS

| | | |
|---|---|---|
| AU | 2017228648 | 6/2019 |
| AU | 2019203924 | 6/2019 |

(Continued)

OTHER PUBLICATIONS

National Center for Biotechnology Information. PubChem Compound Summary for CID 68846177, [2-(6-phenylthieno[3,2-d]pyrimidin-4-yl)pyridin-4-yl]methanamine. Created Nov. 30, 2012. (Year: 2012).*
Dörwald, F. Zaragoza. Side Reactions in Organic Synthesis: A Guide to Successful Synthesis Design, Weinheim: Wiley-VCH Verlag Gmbh & Co. KGaA, 2005, Preface (Year: 2005).*
Van, Hue Thi My, et al. European Journal of Medicinal Chemistry 82 (2014): 181-194. (Year: 2014).*
"Registry (STN)", CAS registration No. 930727-89-2, Apr. 18, 2007.
"Registry (STN)", CAS registration No. 874830-23-6, Feb. 21, 2006.
Campos et al., "The First Catalytic Direct C—H Arylation on C2 and C3 of Thiophene Ring Applied to Thieno-Pyridines, -Pyrimidines and -Pyrazines", Catalysts, vol. 8, No. 4, 2018, 14 pages.

(Continued)

*Primary Examiner* — Matthew P Coughlin
*Assistant Examiner* — Quincy McKoy
(74) *Attorney, Agent, or Firm* — Kilpatrick Townsend & Stockton LLP

(57) ABSTRACT

Provided herein are compositions and methods for treating or preventing a neurodegenerative disease, a myodegenerative disease, a prion disease or a lysosomal storage disease in a subject.

28 Claims, 17 Drawing Sheets

(56) References Cited

U.S. PATENT DOCUMENTS

| | | |
|---|---|---|
| 2014/0350037 A1 | 11/2014 | Szczudlo et al. |
| 2015/0030588 A1 | 1/2015 | Jessen et al. |
| 2015/0087653 A1 | 3/2015 | Moussa |
| 2015/0104467 A1 | 4/2015 | Constantin |
| 2016/0089371 A1 | 3/2016 | Liu et al. |
| 2017/0158706 A1 | 6/2017 | Dorsey et al. |
| 2017/0216287 A1 | 8/2017 | Moussa |

FOREIGN PATENT DOCUMENTS

| | | |
|---|---|---|
| CN | 104204804 A | 12/2014 |
| CN | 104981247 A | 10/2015 |
| CN | 105246482 A | 1/2016 |
| EP | 2844256 | 8/2016 |
| JP | 2005538118 A | 12/2005 |
| JP | 2014533284 A | 12/2014 |
| JP | 2014533728 A | 12/2014 |
| JP | 2015529224 A | 10/2015 |
| JP | 2018521026 A | 8/2018 |
| JP | 2018525429 A | 9/2018 |
| WO | 2004000313 | 12/2003 |
| WO | 2004013141 A1 | 2/2004 |
| WO | 2005039586 A1 | 5/2005 |
| WO | 2006026785 | 3/2006 |
| WO | 2009007422 A1 | 1/2009 |
| WO | 2010017541 | 2/2010 |
| WO | 2011003418 A1 | 1/2011 |
| WO | 2011062927 A1 | 5/2011 |
| WO | 2011097581 | 8/2011 |
| WO | 2012098416 | 7/2012 |
| WO | 2014039714 A2 | 3/2014 |
| WO | 2016201266 A1 | 12/2016 |
| WO | 2017036978 A1 | 3/2017 |
| WO | 2017208267 | 12/2017 |
| WO | 2018148533 A1 | 8/2018 |
| WO | 2018167802 | 2/2019 |

OTHER PUBLICATIONS

CN201980087338.6, "Office Action", Sep. 23, 2023, 10 pages.
JP2021-527905, "Office Action", Oct. 3, 2023, 10 pages.
MX/A/2021/005875, "Office Action", Aug. 25, 2023, 3 pages.
EP19887380.4, "Extended European Search Report", Jul. 11, 2022, 6 pages.
Mohler et al., "Recent and Emerging Anti-Diabetes Targets", Medicinal Research Reviews, vol. 29, No. 1, Jan. 1, 2009, pp. 125-195.
CA3,120,639, "Office Action", Feb. 22, 2024, 4 pages.
CA3134922, "Notice of Allowance", Mar. 14, 2024, 1 page.
MX/A/2021/005875, "Office Action", Feb. 13, 2024, 4 pages.
AU2019385480, "First Examination Report", May 28, 2024, 4 pages.
U.S. Appl. No. 16/909,075, Non-Final Office Action, Mailed on Mar. 2, 2022, 13 pages.
Netzer et al., "Gleevec Inhibits-Amyloid Production but notNotch Cleavage", PNAS, vol. 100, Issue 21, Oct. 14, 2003, pp. 12444-12449.
Shukla et al., "Synthesis and Characterization of a Bodipy Conjugate of the BCR-ABL Kinase Inhibitor Tasigna (Nilotinib): Evidence for Transport of Tasigna and Its Fluorescent Derivative by ABC Drug Transporters", Mol. Pharmaceutics, vol. 8, Issue 4, Aug. 1, 2011, pp. 1292-1302.
"FDA Prescribing Information for Tasigna Capsules", 2010, 35 pages.
U.S. Appl. No. 16/909,075, "Final Office Action", filed Oct. 27, 2022, 19 pages.
Weisberg et al., "Characterization of AMN107, a selective inhibitor of native and mutant Bcr-Abl", Cancer Cell, vol. 7, No. 2, Feb. 2005, pp. 129-141.
IL283271, "Office Action", Dec. 19, 2023, 4 pages.
"[2-(6-Phenylthieno[3,2-d]pyrimidin-4-yl)pyridin-4-yl]methanamine", PubChem CID: 68846177, Available Online at : https://pubchem.ncbi.nlm.nih.gov/compound/68846177, Nov. 30, 2012, 9 pages.
"5-(7-Pyridin-4-Ylthieno[3,2-B]Pyridin-2-yl)-1,3-Benzoxazol-2-Amine", PubChem CID: 68405246, Available Online at: https://pubchem.ncbi.nlm.nih.gov/compound/68405246, Nov. 30, 2012, 9 pages.
"Nilotinib in Cognitively Impaired Parkinson Disease Patients 001", Available Online at: https://clinicaltrials.gov/ct2/show/NCT02281474, Dec. 15, 2015, pp. 1-3.
"Parkinson's Disease: Excess of Special Protein Identified as Key to Symptoms and Possible New Target for Treatment with Widely Used Anti-Cancer Drug", Johns Hopkins Medicine, Available Online at: http://www.hopkinsmedicine.org/news/media/releases/parkinsons_disease_excess_of_special_protein_identified_as_key_to_symptoms_and_possible_new_target_for_treatment_with_widely_used_anti_cancer_drug, Sep. 30, 2010, 2 pages.
"San Antonio Researchers Hope Leukemia Drug Could Treat Parkinson's", Available Online at: http://www.kens5.com/home/Leukemia-drug-may-help-treat-Parkinsons-disease-113295119.html, Nov. 8, 2013, 3 pages.
Abouantoun et al., "Sunitinib Induces PTEN Expression and Inhibits PDGFR Signaling and Migration of Medulloblastoma Cells", Journal of Neurooncology, vol. 101, No. 2, Jan. 2011, pp. 215-226.
Alvarez et al., "Activation of the Neuronal C-Abl Tyrosine Kinase by Amyloid-Beta-Peptide and Reactive Oxygen Species", Neurobiology of Disease, vol. 17, No. 2, Nov. 2004, pp. 326-336.
Avraham et al., "Phosphorylation of Parkin by the Cyclin-Dependent Kinase 5 at the Linker Region Modulates Its Ubiquitin-Ligase Activity and Aggregation", Journal of Biological Chemistry, vol. 282, No. 17, Apr. 27, 2007, pp. 12842-12850.
Bazzu et al., "α-Synuclein- and MPTP-Generated Rodent Models of Parkinsons Disease and the Study of Extracellular Striatal Dopamine Dynamics: A Microdialysis Approach", CNS & Neurological Disorders—Drug Targets, vol. 9, Issue 4, Aug. 2010, pp. 482-490.
Bellodi et al., "Targeting Autophagy Potentiates Tyrosine Kinase Inhibitor-Induced Cell Death in Philadelphia Chromosome-Positive Cells, Including Primary CML Stem Cells", Journal of Clinical Investigation, vol. 119, No. 5, May 2009, pp. 1109-1123.
Benner et al., "Nitrated α-Synuclein Immunity Accelerates Degeneration of Nigral Dopaminergic Neurons", PLoS One, Issue 1, Jan. 2008, pp. 1-20.
Bjorkoy et al., "p62/SQSTM1 Forms Protein Aggregates Degraded by Autophagy and Has a Protective Effect on Huntingtin-Induced Cell Death", Journal of Cell Biology, vol. 171, No. 4, Nov. 21, 2005, pp. 603-614.
Boland et al., "Autophagy Induction and Autophagosome Clearance in Neurons: Relationship to Autophagic Pathology in Alzheimer's Disease", The Journal of Neuroscience, vol. 28, No. 27, Jul. 2, 2008, pp. 6926-6937.
Braak et al., "Staging of Alzheimer's Disease-Related Neurofibrillary Changes", Neurobiology of Aging, vol. 16, Issue 3, May-Jun. 1995, pp. 271-278.
Burns et al., "Parkin Promotes Intracellular Aβ1-42 Clearance", Human Molecular Genetics, vol. 18, Issue 17, 2009, pp. 3206-3216.
Cancino et al., "C-Abl Tyrosine Kinase Modulates Tau Pathology and Cdk5 Phosphorylation in AD Transgenic Mice", Neurobiology of Aging, vol. 32, Issue 7, Jul. 2011, pp. 1249-1261.
Cancino et al., "STI571 Prevents Apoptosis, Tau Phosphorylation and Behavioural Impairments Induced by Alzheimer's β-Amyloid Deposits", Brain, vol. 131, Issue 9, Sep. 2008, pp. 2425-2442.
Chabrol et al., "X-Linked Myopathy with Excessive Autophagy: A Clinicopathological Study of Five New Families", Neuromuscular Disorders, vol. 11, Issue 4, May 2001, pp. 376-388.
Chen et al., "Parkin Mono-Ubiquitinates Bcl-2 and Regulates Autophagy", Journal of Biological Chemistry, vol. 285, No. 49, Dec. 3, 2010, pp. 38214-38223.
Chu, "Autophagic Stress in Neuronal Injury and Disease", Journal of Neuropathology & Experimental Neurology, vol. 65, Issue 5, May 2006, pp. 423-432.
Clark et al., "*Drosophila* Pink1 is Required for Mitochondrial Function and Interacts Genetically with Parkin", Nature, vol. 441, 2006, pp. 1162-1166.
Cook et al., "Alzheimer's Aβ(1-42) is Generated in the Endoplasmic Reticulum/Intermediate Compartment of NT2N Cells", Nature Medicine, vol. 3, No. 9, Sep. 1997, pp. 1021-1023.

(56) References Cited

OTHER PUBLICATIONS

Cookson et al., "Parkinson's Disease: Insights from Pathways", Human Molecular Genetics, vol. 19, Issue R1, Apr. 15, 2010, pp. R21-R27.
Cookson et al., "Ring Finger 1 Mutations in Parkin Produce Altered Localization of the Protein", Human Molecular Genetics, vol. 12, No. 22, 2003, pp. 2957-2965.
Cuervo et al., "Impaired Degradation of Mutant Alpha-Synuclein by Chaperone-Mediated Autophagy", Science, vol. 305, Issue 5688, Aug. 27, 2004, pp. 1292-1295.
D'Andrea et al., "Evidence that Neurones Accumulating Amyloid can Undergo Lysis to Form Amyloid Plaques in Alzheimer's Disease", Histopathology, vol. 38, Issue 2, Feb. 2001, pp. 120-134.
D'Hooge et al., "Applications of the Morris Water Maze in the Study of Learning and Memory", Brain Research Reviews, vol. 36, Issue 1, Aug. 2001, pp. 60-90.
Davis, "Early-Onset and Robust Cerebral Microvascular Accumulation of Amyloid β-Protein in Transgenic Mice Expressing Low Levels of a Vasculotropic Dutch/Iowa Mutant Form of Amyloid β-Protein Precursor", Journal of Biological Chemistry, vol. 279, No. 19, 2004, pp. 20296-20306.
De Duve et al., "Functions of Lysosomes", Annual Review of Physiology, vol. 28, Mar. 1966, pp. 435-492.
Deremer et al., "Nilotinib: A Second-Generation Tyrosine Kinase Inhibitor for the Treatment of Chronic Myelogenous Leukemia", Clinical Therapeutics, vol. 30, No. 11, Nov. 2008, pp. 1956-1975.
Derkinderen et al., "Tyrosine 394 is Phosphorylated in Alzheimer's Paired Helical Filament Tau and in Fetal Tau with c-Abl as the Candidate Tyrosine Kinase", The Journal of Neuroscience, vol. 25, No. 28, Jul. 13, 2005, pp. 6584-6593.
Ding et al., "Histone Deacetylase 6 Interacts with the Microtubule-Associated Protein Tau", Journal of Neurochemistry, vol. 106, Issue 5, Sep. 2008, pp. 2119-2130.
Dunn, "Autophagy and Related Mechanisms of Lysosome-Mediated Protein Degradation", Trends in Cell Biology, vol. 4, Issue 4, Apr. 1994, pp. 139-143.
Durcan et al., "Mutant Ataxin-3 Promotes the Autophagic Degradation of Parkin", Autophagy, vol. 7, Issue 2, 2011, pp. 233-234.
Durcan et al., "The Machado-Joseph Disease-Associated Mutant Form of Ataxin-3 Regulates Parkin Ubiquitination and Stability", Human Molecular Genetics, vol. 20, No. 1, Jan. 1, 2011, pp. 141-154.
Ertmer et al., "The Anticancer Drug Imatinib Induces Cellular Autophagy", Leukemia, vol. 21, Mar. 2007, pp. 936-942.
Eskelinen, "Maturation of Autophagic Vacuoles in Mammalian Cells", Autophagy, vol. 1, No. 1, Apr. 2005, pp. 1-10.
Gasser et al., "Molecular Pathogenesis of Parkinson Disease: Insights from Genetic Studies", Expert Reviews in Molecular Medicine, vol. 11, e22, Jul. 2009, pp. 1-19.
Geisler et al., "PINK1/Parkin-Mediated Mitophagy is Dependent on VDAC1 and P62/SQSTM1", Nature Cell Biology, vol. 12, No. 2, Feb. 2010, pp. 119-131.
Giasson et al., "Neuronal α-Synucleinopathy with Severe Movement Disorder in Mice Expressing A53T Human α-Synuclein", Neuron, vol. 34, Issue 4, May 16, 2002, pp. 521-533.
Goedert, "Alpha-Synuclein and Neurodegenerative Diseases", Nature Reviews Neuroscience, vol. 2, Jul. 2001, pp. 492-501.
Goedert, "Filamentous Nerve Cell Inclusions in Neurodegenerative Diseases: Tauopathies and Alphasynucleinopathies", Philosophical Transactions of the Royal Society B: Biological Sciences, vol. 354, Jun. 1999, pp. 1101-1118.
Gonzalez-Polo et al., "The Apoptosis/Autophagy Paradox: Autophagic Vacuolization Before Apoptotic Death", Journal of Cell Science, vol. 118, No. 14, 2005, pp. 3091-3102.
Gordon et al., "Prelysosomal Convergence of Autophagic and Endocytic Pathways", Biochemical and Biophysical Research Communications, vol. 151, Issue 1, Feb. 29, 1988, pp. 40-47.
Gordon et al., "Tyrosine Kinase Inhibitors in the Treatment of Systemic Sclerosis: The Difficulty in Interpreting Proof-of-Concept Studies", International Journal of Clinical Rheumatology, vol. 2011, 2011, pp. 1-8.
Gouras et al., "Intraneuronal Aβ42 Accumulation in Human Brain", The American Journal of Pathology, vol. 156, Issue 1, Jan. 2000, pp. 15-20.
Greene et al., "Mitochondrial Pathology and Apoptotic Muscle Degeneration in *Drosophila* Parkin Mutants", Proceedings of the National Academy of Sciences of the United States of America, vol. 100, No. 7, Apr. 1, 2003, pp. 4078-4083.
Greenfield et al., "Endoplasmic Reticulum and Trans-Golgi Network Generate Distinct Populations of Alzheimer β-Amyloid Peptides", Proceedings of the National Academy of Sciences of the United States of America, vol. 96, No. 2, Jan. 19, 1999, pp. 742-747.
Hampe et al., "Biochemical Analysis of Parkinson's Disease-Causing Variants of Parkin, An E3 Ubiquitin-Protein Ligase with Monoubiquitylation Capacity", Human Molecular Genetics, vol. 15, No. 13, 2006, pp. 2059-2075.
Hara et al., "Suppression of Basal Autophagy in Neural Cells Causes Neurodegenerative Disease in Mice", Nature, vol. 441, 2006, pp. 885-889.
Hardy et al., "The Amyloid Hypothesis of Alzheimer's Disease: Progress and Problems on the Road to Therapeutics", Science, vol. 297, Issue 5580, 2002, pp. 353-356.
Hasegawa et al., "Phosphorylated TDP-43 in Frontotemporal Lobar Degeneration and Amyotrophic Lateral Sclerosis", Annals of Neurology, vol. 64, No. 1, Jul. 2008, pp. 60-70.
He et al., "Gamma-Secretase Activating Protein, A Therapeutic Target for Alzheimer's Disease", Nature, vol. 467, No. 7311, Sep. 2, 2010, 13 pages.
He et al., "Post-Translational Modifications of Three Members of the Human MAP1LC3 Family and Detection of a Novel Type of Modification for MAP1LC3B", Journal of Biological Chemistry, vol. 278, No. 31, 2003, pp. 29278-29287.
He et al., "Regulation Mechanisms and Signaling Pathways of Autophagy", Annual Review of Genetics, vol. 43, 2009, 29 pages.
Healy et al., "Tau Gene and Parkinson's Disease: A Case-control Study and Meta-Analysis", Journal of Neurology, Neurosurgery, and Psychiatry, vol. 75, Issue 7, 2004, pp. 962-965.
Hebron et al., "Nilotinib Reverses Loss of Dopamine Neurons and Improves Motor Behavior via Autophagic Degradation of α-Synuclein in Parkinson's Disease Models", Human Molecular Genetics, vol. 22, No. 16, Aug. 15, 2013, pp. 3315-3328.
Hebron et al., "Two Sides of the Same Coin: Tyrosine Kinase Inhibition in Cancer and Neurodegeneration", Neural Regeneration Research, vol. 10, Issue 11, Nov. 2015, pp. 1767-1769.
Hebron et al., "Tyrosine Kinase Inhibition Facilitates Autophagic SNCA/α-Synuclein Clearance", Autophagy, vol. 9, No. 8, Aug. 2013, pp. 1249-1250.
Helgason et al., "Kill One Bird with Two Stones: Potential Efficacy of BCR-ABL and Autophagy Inhibition in CML", Blood, vol. 118, No. 8, Aug. 25, 2011, pp. 2035-2043.
Henn et al., "Pathogenic Mutations Inactivate Parkin by Distinct Mechanisms", Journal of Neurochemistry, vol. 92, Issue 1, Jan. 2005, pp. 114-122.
Herman et al., "The Ubiquitin Ligase Parkin Modulates the Execution of Autophagy", Autophagy, vol. 7, No. 8, Aug. 2011, pp. 919-921.
Huang et al., "The Itinerary of a Vesicle Component, Aut7p/Cvt5p, Terminates in the Yeast Vacuole via the Autophagy/Cvt Pathways", Journal of Biological Chemistry, vol. 275, No. 8, Feb. 25, 2000, pp. 5845-5851.
Imam et al., "Novel Regulation of Parkin Function through c-Abl-Mediated Tyrosine Phosphorylation: Implications for Parkinson's Disease", The Journal of Neuroscience, vol. 31, No. 1, Jan. 5, 2011, pp. 157-163.
Iwata et al., "HDAC6 and Microtubules Are Required for Autophagic Degradation of Aggregated Huntingtin", The Journal of Biological Chemistry, vol. 280, No. 48, Dec. 2, 2005, pp. 40282-40292.
Jing et al., "Altered Subcellular Distribution of c-Abl in Alzheimer's Disease", Journal of Alzheimer's Disease, vol. 17, No. 2, Jun. 2009, 22 pages.

(56) References Cited

OTHER PUBLICATIONS

Kanki et al., "Atg32 is a Mitochondrial Protein that Confers Selectivity During Mitophagy", Developmental Cell, vol. 17, Issue 1, Jul. 2009, 21 pages.
Kantarjian et al., "Hematologic and Cytogenetic Responses to Imatinib Mesylate in Chronic Myelogenous Leukemia", The New England Journal of Medicine, vol. 346, No. 9, Feb. 28, 2002, pp. 645-652.
Karuppagounder et al., "Nilotinib, A cAb1 Inhibitor, Protects Dopaminergic Neurons from M PTP Induced Neurotoxicity", Neuroscience Program, Poster 883.02/Y1, 2011, 1 page.
Karuppagounder et al., "The c-Abl Inhibitor, Nilotinib, Protects Dopaminergic Neurons in a Preclinical Animal Model of Parkinson's Disease", Scientific Reports, vol. 4, Article No. 4874, May 2, 2014, pp. 1-8.
Katsumata et al., "c-Abl Inhibition Delays Motor Neuron Degeneration in the G93A Mouse, an Animal Model of Amyotrophic Lateral Sclerosis", Public Library of Science One, vol. 7, No. 9, Sep. 2012, pp. 1-14.
Kawahara et al., "α-Synuclein Aggregates Interfere with Parkin Solubility and Distribution: Role in the Pathogenesis of Parkinson Disease", Journal of Biological Chemistry, vol. 283, No. 11, Mar. 14, 2008, pp. 6979-6987.
Kegel et al., "Huntington Expression Stimulates Endosomal-Lysosomal Activity, Endosome Tubulation, and Autophagy", The Journal of Neuroscience, vol. 20, No. 19, Oct. 1, 2000, pp. 7268-7278.
Khandelwal et al., "Parkin Mediates Beclin-Dependent Autophagic Clearance of Defective Mitochondria and Ubiquitinated Aβ in AD Models", Human Molecular Genetics, vol. 20, Issue 11, Jun. 1, 2011, pp. 2091-2102.
Khandelwal et al., "Parkinson-Related Parkin Reduces Alpha-Synuclein Phosphorylation in a Gene Transfer Model", Molecular Neurodegeneration, vol. 5, No. 47, 2010, pp. 1-13.
Khandelwal et al., "Wild Type and P301L Mutant Tau Promote Neuro-Inflammation and α-Synuclein Accumulation in Lentiviral Gene Delivery Models", Molecular and Cellular Neuroscience, vol. 49, No. 1, Jan. 2012, 22 pages.
Kim et al., "Pink1 Controls Mitochondrial Localization of Parkin Through Direct Phosphorylation", Biochemical and Biophysical Research Communications, vol. 377, No. 3, 2008, pp. 975-980.
Kirik et al., "Parkinson-Like Neurodegeneration Induced by Targeted Overexpression of Alpha-Synuclein in the Nigrostriatal System", The Journal of Neuroscience, vol. 22, No. 7, Apr. 1, 2002, pp. 2780-2791.
Kirkin et al., "A Role for Ubiquitin in Selective Autophagy", Molecular Cell, vol. 34, May 15, 2009, pp. 259-269.
Kitada et al., "Mutations in the Parkin Gene Cause Autosomal Recessive Juvenile Parkinsonism", Nature, vol. 392, Apr. 9, 1998, pp. 605-608.
Ko et al., "Phosphorylation by the C-Abl Protein Tyrosine Kinase Inhibits Parkin's Ubiquitination and Protective Function", Public Library of Science, vol. 107, No. 38, Sep. 21, 2010, pp. 16691-16696.
Koike et al., "Participation of Autophagy in Storage of Lysosomes in Neurons from Mouse Models of Neuronal Ceroid-Lipofuscinoses (Batten Disease)", American Journal of Pathology, vol. 167, No. 6, Dec. 2005, pp. 1713-1728.
Komatsu et al., "Loss of Autophagy in the Central Nervous System Causes Neurodegeneration in Mice", Nature, vol. 441, Jun. 15, 2006, pp. 880-884.
Kovacs et al., "Accumulation of Autophagosomes After Inhibition of Hepatocytic Protein Degradation by Vinblastine, Leupeptin or a Lysosomotropic Amine", Experimental Cell Research, vol. 137, Issue 1, Jan. 1982, pp. 191-201.
Krakstad et al., "Survival Signalling and Apoptosis Resistance in Glioblastomas: Opportunities for Targeted Therapeuticus", Molecular Cancer, vol. 9, Article No. 135, Jun. 2010, pp. 1-14.
Kuhn et al., "Dopamine Quinones Activate Microglia and Induce a Neurotoxic Gene Expression Profile: Relationship to Methamphetamine-Induced Nerve Ending Damage", Annals of the New York Academy of Sciences, vol. 1074, Issue 1, Aug. 2006, pp. 31-41.
Li et al., "Mice Deficient in Abl are Osteoporotic and Have Defects in Osteoblast Maturation", Nature Genetics, vol. 24, Mar. 2000, pp. 304-308.
Li et al., "The Role of Intracellular Amyloid β in Alzheimer's Disease", Progress in Neurobiology, vol. 83, Issue 3, Oct. 2007, pp. 131-139.
Liu et al., "Inhibitors of LRRK2 Kinase Attenuate Neurodegeneration and Parkinson-Like Phenotypes in Caenorhabditis Elegans and *Drosophila* Parkinson's Disease Models", Human Molecular Genetics, vol. 20, Issue 20, 2011, pp. 3933-3942.
Lonskaya et al., "Decreased Parkin Solubility is Associated with Impairment of Autophagy in the Nigrostriatum of Sporadic Parkinson's Disease", Neuroscience, vol. 232, Mar. 1, 2013, 29 pages.
Lonskaya et al., "Diminished Parkin Solubility and Co-Localization with Intraneuronal Amyloid-β are Associated with Autophagic Defects in Alzheimer's Disease", Journal of Alzheimer's Disease, vol. 33, No. 1, Sep. 6, 2012, pp. 231-247.
Lonskaya et al., "Nilotinib and Bosutinib Modulate Pre-Plaque Alterations of Blood Immune Markers and Neuroinflammation in Alzheimer's Disease Models", Neuroscience, vol. 304, Sep. 24, 2015, pp. 316-327.
Lonskaya et al., "Nilotinib-Induced Autophagic Changes Increase Endogenous Parkin Level and Ubiquitination, Leading to Amyloid Clearance", Journal of Molecular Medicine, vol. 92, No. 4, Apr. 2014, 26 pages.
Lonskaya et al., "Tyrosine Kinase Inhibition Increases Functional Parkin-Beclin-1 Interaction and Enhances Amyloid Clearance and Cognitive Performance", EMBO Molecular Medicine, vol. 5, No. 8, Aug. 2013, pp. 1247-1262.
Lucking et al., "Association Between Early-Onset Parkinson's Disease and Mutations in the Parkin Gene", The New England Journal of Medicine, vol. 342, No. 21, May 25, 2000, pp. 1560-1567.
Lundvig et al., "Pathogenic Effects of α-Synuclein Aggregation", Molecular Brain Research, vol. 134, Issue 1, Mar. 24, 2005, pp. 3-17.
Mahon et al., "Evidence that Resistance to Nilotinib May be Due to BCR-ABL, Pgp, or Src Kinase Overexpression", Cancer Research, vol. 68, No. 23, Dec. 1, 2008, pp. 9809-9816.
Malkus et al., "Regional Deficiencies in Chaperone-mediated Autophagy Underlie α-Synuclein Aggregation and Neurodegeneration", Neurobiology of Disease, vol. 46, Issue 3, Jun. 2012, 25 pages.
Martin et al., "Association of Single-Nucleotide Polymorphisms of the Tau Gene with Late-Onset Parkinson Disease", JAMA, vol. 286, No. 18, Nov. 2001, 11 pages.
Martinez-Vicente et al., "Dopamine-Modified α-Synuclein Blocks Chaperone-Mediated Autophagy", The Journal of Clinical Investigation, vol. 118, No. 2, Feb. 2008, pp. 777-788.
Martin-Villalba et al., "Therapeutic Neutralization of CD95-Ligand and TNF Attenuates Brain Damage in Stroke", Cell Death & Differentiation, vol. 8, No. 7, 2001, pp. 679-686.
Marzella et al., "Isolation of Autophagic Vacuoles from Rat Liver: Morphological and Biochemical Characterization", Journal of Cell Biology, vol. 93, No. 1, Apr. 1, 1982, pp. 144-154.
McCormack et al., "α-Synuclein Suppression by Targeted Small Interfering RNA in the Primate Substantia Nigra", PLoS One, vol. 5, Issue 8, e12122, Aug. 2010, pp. 1-8.
Mizuno et al., "Parkin and Parkinson's Disease", Current Opinion in Neurology, vol. 14, No. 4, Aug. 2001, pp. 477-482.
Mizushima et al., "Autophagy Fights Disease Through Cellular Self-Digestion", Nature, vol. 451, No. 7182, Feb. 28, 2008, 14 pages.
Mizushima et al., "How to Interpret LC3 Immunoblotting", Autophagy, vol. 3, No. 6, Nov./Dec. 2007, pp. 542-545.
Mizushima et al., "In Vivo Analysis of Autophagy in Response to Nutrient Starvation Using Transgenic Mice Expressing a Fluorescent Autophagosome Marker", Molecular Biology of the Cell, vol. 15, Mar. 2004, pp. 1101-1111.
Morrison et al., "A Simple Cell Based Assay to Measure Parkin Activity", Journal of Neurochemistry, vol. 116, Issue 3, Feb. 2011, pp. 342-349.

(56) References Cited

OTHER PUBLICATIONS

Moussa et al., "Cancer Drug Improved Cognition and Motor Skills in Small Parkinson's Clinical Trial", Available Online at: https://gumc.georgetown.edu/news/Cancer-Drug-Improved-Cognition-and-Motor-Skills-in-Small-Parkinsons-Clinical-Trial, Oct. 17, 2015, pp. 1-4.
Narendra et al., "Parkin is Recruited Selectively to Impaired Mitochondria and Promotes their Autophagy", Journal of Cell Biology, vol. 183, No. 5, Nov. 24, 2008, pp. 795-803.
Narendra et al., "PINK1 is Selectively Stabilized on Impaired Mitochondria to Activate Parkin", PLoS Biol., vol. 8, No. 1, 2010, 21 pages.
Nixon et al., "Autophagy Failure in Alzheimer's Disease-Locating the Primary Defect", Neurobiology of Disease, vol. 43, Issue 1, Jul. 2011, 17 pages.
Nixon et al., "Extensive Involvement of Autophagy in Alzheimer Disease: An Immuno-Electron Microscopy Study", Journal of Neuropathology & Experimental Neurology, vol. 64, No. 2, Feb. 2005, pp. 113-122.
Nixon et al., "Neurodegenerative Lysosomal Disorders: A Continuum from Development to Late Age", Autophagy, vol. 4, Issue 5, Jul. 2008, pp. 1-10.
Novak et al., "Nix is a Selective Autophagy Receptor for Mitochondrial Clearance", EMBO Reports, vol. 11, Issue 1, Jan. 1, 2010, pp. 45-51.
Oddo et al., "Amyloid Deposition Precedes Tangle Formation in a Triple Transgenic Model of Alzheimer's Disease", Neurobiology of Aging, vol. 24, Issue 8, Dec. 2003, pp. 1063-1070.
Okamoto et al., "Mitochondria-Anchored Receptor Atg32 Mediates Degradation of Mitochondria via Selective Autophagy", Development Cell, vol. 17, Issue 1, Jul. 21, 2009, pp. 87-97.
Orvedahl et al., "Image-Based Genome-Wide Sirna Screen Identifies Selective Autophagy Factors", Nature, vol. 480, No. 7375, Dec. 1, 2011, 13 pages.
Pan et al., "The Role of Autophagy-Lysosome Pathway in Neurodegeneration Associated with Parkinson's Disease", Brain, vol. 131, 2008, pp. 1969-1978.
Park et al., "Mitochondrial Dysfunction and Parkinson's Disease Genes: Insights from *Drosophila*", Disease Models & Mechanisms, vol. 2, Jul.-Aug. 2009, pp. 336-340.
Park et al., "Mitochondrial Dysfunction in *Drosophila* PINK1 Mutants is Complemented by Parkin", Nature, vol. 441, No. 7097, Jun. 29, 2006, pp. 1157-1161.
Application No. PCT/US2019/062387, International Preliminary Report on Patentability, Mailed on Jun. 3, 2021, 8 pages.
Application No. PCT/US2019/062387, International Search Report and Written Opinion, Mailed on Mar. 23, 2020, 11 pages.
Perez et al., "Tau—An Inhibitor of Deacetylase HDAC6 Function", Journal of Neurochemistry, vol. 109, Issue 6, Jun. 2009, pp. 1756-1766.
Perucho et al., "The Effects of Parkin Suppression on the Behaviour, Amyloid Processing, and Cell Survival in App Mutant Transgenic Mice", Experimental Neurology, vol. 221, Issue 1, Jan. 2010, pp. 54-67.
Pickford et al., "The Autophagy-Related Protein Beclin 1 Shows Reduced Expression in Early Alzheimer Disease and Regulates Amyloid β Accumulation in Mice", The Journal of Clinical Investigation, vol. 118, No. 6, Jun. 2008, pp. 2190-2199.
Porkka et al., "Dasatinib Crosses the Blood-Brain Barrier and is an Efficient Therapy for Central Nervous System Philadelphia Chromosome-Positive Leukemia", Blood, vol. 112, No. 4, Aug. 15, 2008, pp. 1005-1012.
Qiu et al., "c-Abl Tyrosine Kinase Regulates Cardiac Growth and Development", Proceedings of the National Academy of Sciences of the United States of America, vol. 107, No. 3, Jan. 19, 2010, pp. 1136-1141.
Ravikumar et al., "Aggregate-prone Proteins with Polyglutamine and Polyalanine Expansions are Degraded by Autophagy", Human Molecular Genetics, vol. 11, Issue 9, May 1, 2002, pp. 1107-1117.

Ravikumar et al., "Inhibition of mTOR Induces Autophagy and Reduces Toxicity of Polyglutamine Expansions in Fly and Mouse Models of Huntington Disease", Nature Genetics, vol. 36, 2004, pp. 585-595.
Rebeck et al., "β-Amyloid1—42 Gene Transfer Model Exhibits Intraneuronal Amyloid, Gliosis, Tau Phosphorylation, and Neuronal Loss", Journal of Biological Chemistry, vol. 285, No. 10, Mar. 5, 2010, pp. 7440-7446.
Recchia et al., "Generation of a α-Synuclein-Based Rat Model of Parkinson's Disease", Neurobiology of Disease, vol. 30, Apr. 2008, pp. 8-18.
Reynolds et al., "Nitrated Alpha-Synuclein and Microglial Neuroregulatory Activities", Journal of Neuroimmune Pharmacology, vol. 3, Issue 2, Jun. 2008, 23 pages.
Rodriguez-Navarro et al., "Parkin Deletion Causes Cerebral and Systemic Amyloidosis in Human Mutated Tau Over-Expressing Mice", Human Molecular Genetics, vol. 17, Issue 20, Oct. 15, 2008, pp. 3128-3143.
Rodriguez-Navarro et al., "Trehalose Ameliorates Dopaminergic and Tau Pathology in Parkin Deleted/Tau Overexpressing Mice Through Autophagy Activation", Neurobiology of Disease, vol. 39, Issue 3, Sep. 2010, pp. 423-438.
Rosen et al., "Parkin Reverses Intracellular β-Amyloid Accumulation and Its Negative Effects on Proteasome Function", Journal of Neuroscience Research, vol. 88, No. 1, Jan. 2010, pp. 167-178.
Rubio De La Torre et al., "Combined Kinase Inhibition Modulates Parkin Inactivation", Human Molecular Genetics, vol. 18, Issue 5, Mar. 1, 2009, pp. 809-823.
Sabatini, "mTOR and Cancer: Insights Into a Complex Relationship", Nature Reviews Cancer, vol. 6, Aug. 2006, 6 pages.
Sarkar et al., "Autophagic Clearance of Aggregate-prone Proteins Associated with Neurodegeneration", Methods in Enzymology, vol. 453, 2009, pp. 83-110.
Sarkar et al., "Small Molecules Enhance Autophagy and Reduce Toxicity in Huntington's Disease Models", Nature Chemical Biology, vol. 3, No. 6, Jun. 2007, pp. 331-338.
Schlatterer et al., "c-Abl in Neurodegenerative Disease", Journal of Molecular Neuroscience, vol. 45, No. 3, Nov. 2011, pp. 445-452.
Schlatterer et al., "Neuronal c-Abl Overexpression Leads to Neuronal Loss and Neuroinflammation in the Mouse Forebrain", Journal of Alzheimer's Disease, vol. 25, No. 1, 2011, pp. 119-133.
Schlossmacher et al., "Parkinson's Disease: Assays for the Ubiquitin Ligase Activity of Neural Parkin", Methods in Molecular Biology, vol. 301, 2005, pp. 351-369.
Schwartzberg et al., "Mice Homozygous for the ablm1 Mutation Show Poor Viability and Depletion of Selected B and T Cell Populations", Cell, vol. 65, Issue 7, Jun. 28, 1991, pp. 1165-1175.
Seglen, "Regulation of Autophagic Protein Degradation in Isolated Liver Cells", Chapter 10, Lysosomes: Their Role in Protein Breakdown, 1987, pp. 369-414.
Sha et al., "Phosphorylation of Parkin by Parkinson Disease-Linked Kinase PINK1 Activates Parkin E3 Ligase Function and NF-kB Signaling", Human Molecular Genetics, vol. 19, Issue 2, Jan. 15, 2010, pp. 352-363.
Shimura et al., "Familial Parkinson Disease Gene Product, Parkin, is a Ubiquitin-Protein Ligase", Nature Genetics, vol. 25, 2000, pp. 302-305.
Skorski, "BCR-ABL1 Kinase: Hunting an Elusive Target with New Weapons", Cell Chemical Biology, vol. 18, No. 11, Nov. 23, 2011, pp. 1352-1353.
Skovronsky et al., "Detection of a Novel Intraneuronal Pool of Insoluble Amyloid β Protein that Accumulates with Time in Culture", Journal of Cell Biology, vol. 141, No. 4, May 1998, pp. 1031-1039.
Spencer et al., "Beclin 1 Gene Transfer Activates Autophagy and Ameliorates the Neurodegenerative Pathology in α-Synuclein Models of Parkinson's and Lewy Body Diseases", The Journal of Neuroscience, vol. 29, Issue 43, Oct. 28, 2009, pp. 13578-13588.
Spillantini et al., "Filamentous α-Synuclein Inclusions Link Multiple System Atrophy with Parkinson's Disease and Dementia with Lewy Bodies", Neuroscience Letters, vol. 251, Issue 3, Jul. 31, 1998, pp. 205-208.

(56) References Cited

OTHER PUBLICATIONS

Spillantini et al., "The α-Synucleinopathies: Parkinson's Disease, Dementia with Lewy Bodies, and Multiple System Atrophy", Annals of the New York Academy of Sciences, vol. 920, Issue 1, Dec. 2000, pp. 16-27.
Spillantini et al., "α-Synuclein in Filamentous Inclusions of Lewy Bodies from Parkinson's Disease and Dementia with Lewy Bodies", PNAS, vol. 95, No. 11, May 26, 1998, pp. 6469-6473.
Spillantini et al., "α-Synuclein in Lewy Bodies", Nature, vol. 388, Aug. 28, 1997, pp. 839-840.
Staropoli et al., "Parkin is a Component of an SCF-Like Ubiquitin Ligase Complex and Protects Postmitotic Neurons from Kainate Excitotoxicity", Neuron, vol. 37, Issue 5, Mar. 6, 2003, pp. 735-749.
Stefanis, "Expression of A53T Mutant But Not Wild-Type α-Synuclein in PC12 Cells Induces Alterations of the Ubiquitin-Dependent Degradation System, Loss of Dopamine Release, and Autophagic Cell Death", The Journal of Neuroscience, vol. 21, No. 24, Dec. 15, 2001, pp. 9549-9560.
Sutovsky et al., "Ubiquitin Tag for Sperm Mitochondria", Nature, vol. 402, No. 6760, Nov. 25, 1999, pp. 371-372.
Takeda et al., "C-Terminal α-Synuclein Immunoreactivity in Structures Other Than Lewy Bodies in Neurodegenerative Disorders", Acta Neuropathologica, vol. 99, Issue 3, Jan. 2000, pp. 296-304.
Tan et al., "Lysine 63-Linked Polyubiquitin Potentially Partners with P62 to Promote the Clearance of Protein Inclusions by Autophagy", Autophagy, vol. 4, Issue 2, Feb. 16, 2008, pp. 251-253.
Tanabe et al., "A Novel Tyrosine Kinase Inhibitor AMN107 (Nilotinib) Normalizes Striatal Motor Behaviors in a Mouse Model of Parkinson's Disease", Frontiers in Cellular Neuroscience, vol. 8, Article 50, Feb. 2014, pp. 1-9.
Thiruchelvam et al., "Risk Factors for Dopaminergic Neuron Loss in Human α-Synuclein Transgenic Mice", European Journal of Neuroscience, vol. 19, Issue 4, Feb. 2004, pp. 845-854.
Tremblay et al., "Tau Phosphorylated at Tyrosine 394 is Found in Alzheimer's Disease Tangles and Can be a Product of the Abl-Related Kinase, Arg", Journal of Alzheimer's Disease, vol. 19, No. 2, 2010, pp. 721-733.
Trojanowski et al., "Parkinson's Disease and Related α-Synucleinopathies are Brain Amyloidoses", Annals of the New York Academy of Sciences, vol. 991, 2003, pp. 107-110.
Tybulewicz et al., "Neonatal Lethality and Lymphopenia in Mice with a Homozygous Disruption of the c-Abl Proto-Oncogene", Cell, vol. 65, Jun. 28, 1991, pp. 1153-1163.
Mves-Bauza et al., "PINK1-Dependent Recruitment of Parkin to Mitochondria in Mitophagy", PNAS, vol. 107, No. 1, Jan. 5, 2010, pp. 378-383.
Wakabayashi et al., "NACP, A Presynaptic Protein, Immunoreactivity in Lewy Bodies in Parkinson's Disease", Neuroscience Letters, vol. 239, 1997, pp. 45-48.
Walton, "A Cancer Drug may help treat Alzheimer's and other forms of Dementia", Forbes, Pharma & Healthcare, Available Online at: http://www.forbes.com/sites/alicegwalton/2013/05/10/do-we-have-another-drug-candidate-for-alzheimers-and-dementia/#7f5bd50d2806, May 10, 2013, 5 pages.
Wang et al., "Nilotinib Induced Remission of Central Nervous System Relapse of Imatinib-Resistant PH+ CML After Allogeneic Haematopoietic Cell Transplantation", Minimal Residual Disease, Available Online at: http://registration.akm.ch/einsicht.phpXNABSTRACT_ID=105837&XNSPRACHE_ID=2&XNKONGRESS_ID=110&XNMASKEN_ID=900, Mar. 22, 2010, 1 page.
Wang et al., "Regulation of Cell Death by the Abl Tyrosine Kinase", Oncogene, vol. 19, 2000, pp. 5643-5650.
Webb et al., "Alpha-Synuclein is Degraded by Both Autophagy and the Proteasome", Journal of Biological Chemistry, vol. 278, No. 27, Jul. 4, 2003, pp. 25009-25013.
Wenzel et al., "UBCH7 Reactivity Profile Reveals Parkin and HHARI to be RING/HECT Hybrids", Nature, vol. 474, No. 7349, Jun. 2, 2011, pp. 105-108.
Wild et al., "Mitochondria Get a Parkin' Ticket", Nature Cell Biology, vol. 12, 2010, pp. 104-106.
Wilson et al., "Intracellular APP Processing and A β Production in Alzheimer Disease", Journal of Neuropathology & Experimental Neurology, vol. 58, Issue 8, Aug. 1999, pp. 787-794.
Winslow et al., "Autophagy in Neurodegeneration and Development", Biochimica et Biophysica Acta, vol. 1782, 2008, pp. 723-729.
Winslow et al., "The Parkinson Disease Protein α-Synuclein Inhibits Autophagy", Autophagy, vol. 7, No. 4, Apr. 2011, pp. 429-431.
Winslow et al., "α-Synuclein Impairs Macroautophagy: Implications for Parkinson's Disease", Journal of Cell Biology, vol. 190, Sep. 20, 2010, pp. 1023-1037.
Xilouri et al., "Abberant α-Synuclein Confers Toxicity to Neurons in Part Through Inhibition of Chaperone-Mediated Autophagy", PLoS One, vol. 4, Issue 5, e5515, May 2009, pp. 1-15.
Xu et al., "Generation of Alzheimer β-Amyloid Protein in the Trans-Golgi Network in the Apparent Absence of Vesicle Formation", PNAS, vol. 94, Apr. 1997, pp. 3748-3752.
Yamada et al., "Parkin Gene Therapy for α-Synucleinopathy: A Rat Model of Parkinson's Disease", Human Gene Therapy, vol. 16, No. 2, Feb. 2005, pp. 262-270.
Yamamoto et al., "Parkin Phosphorylation and Modulation of Its E3 Ubiquitin Ligase Activity", Journal of Biological Chemistry, vol. 280, No. 5, Feb. 4, 2005, pp. 3390-3399.
Yang et al., "Induction of Autophagy in Neurite Degeneration of Mouse Superior Cervical Ganglion Neurons", European Journal of Neuroscience, vol. 26, 2007, pp. 2979-2988.
Yokoseki et al., "TDP-43 Mutation in Familial Amyotrophic Lateral Sclerosis", Annals of Neurology, vol. 63, No. 4, Apr. 2008, pp. 538-542.
AU2020286230 "Notice of Acceptance", May 4, 2023, 3 pages.
CA3134922 "Office Action", Jun. 12, 2023, 5 pages.
EP23157839.4, "Extended European Search Report", Aug. 8, 2023, 10 pages.
CN201980087338.6, "Office Action", Jun. 29, 2024, 5 pages.
JP2021-527905, "Office Action", Jun. 6, 2024, 3 pages.
MX/A/2021/005875, "Office Action", Jun. 10, 2024, 4 pages.
CA3,120,639, "Office Action", Oct. 1, 2024, 3 pages.
MX/A/2021/005875, "Office Action", Sep. 11, 2024, 9 pages.

* cited by examiner

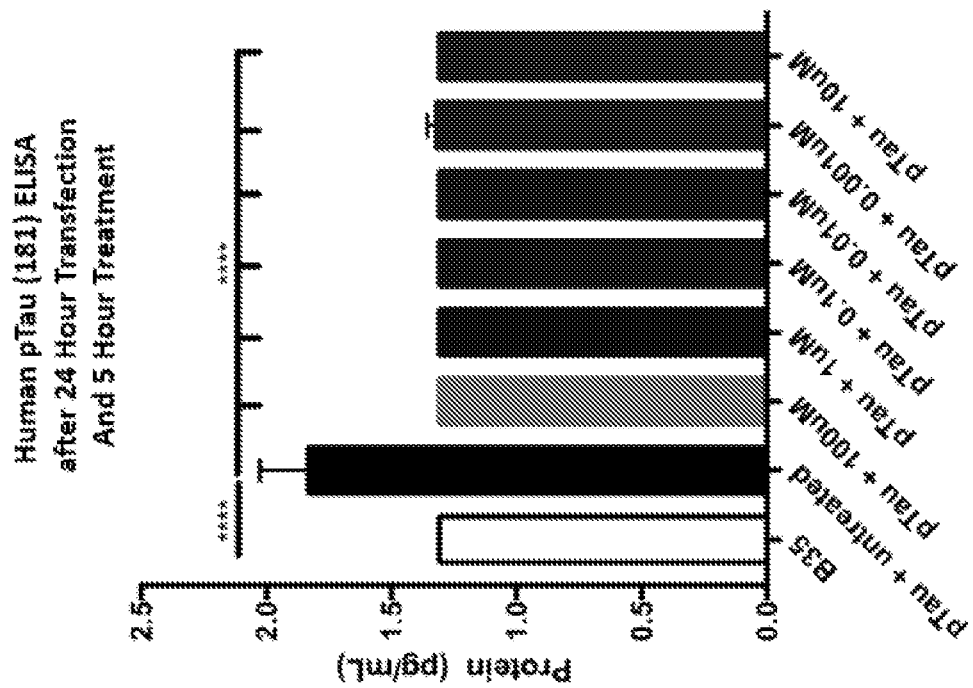
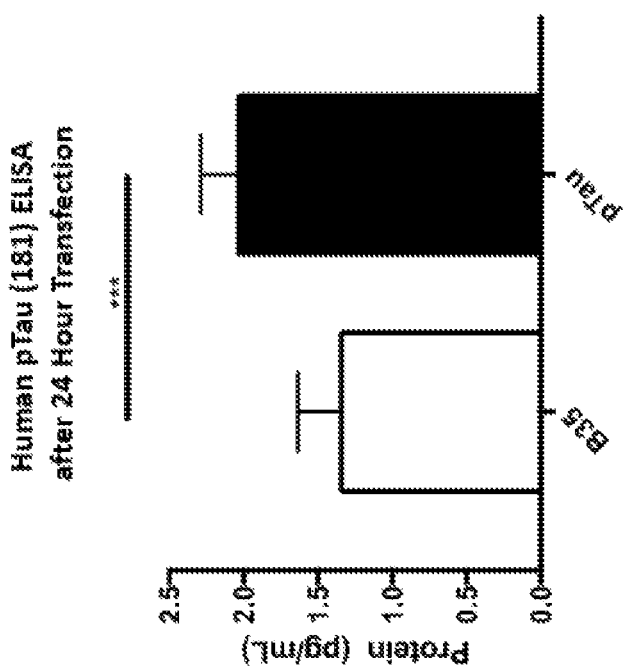
FIG. 3

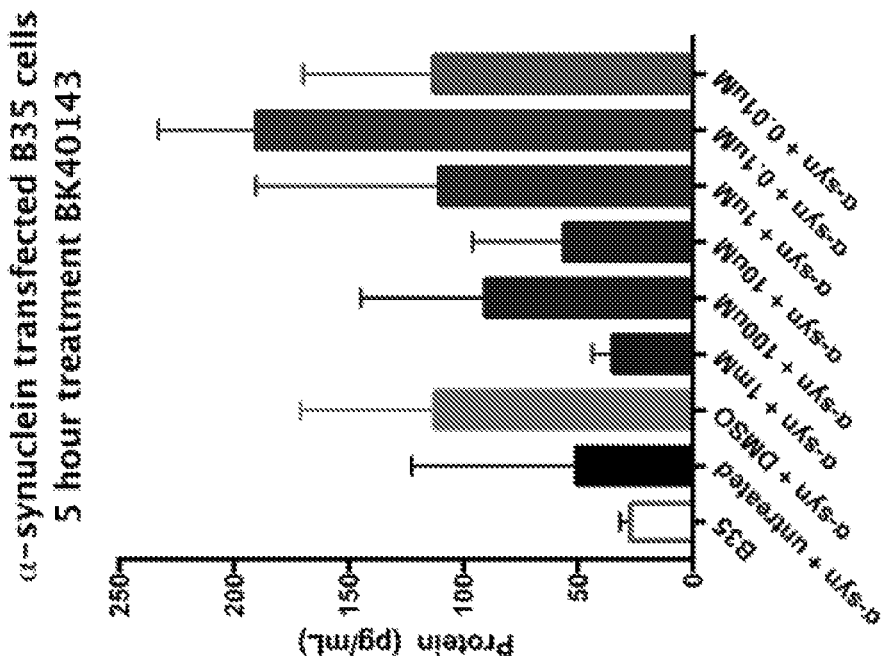
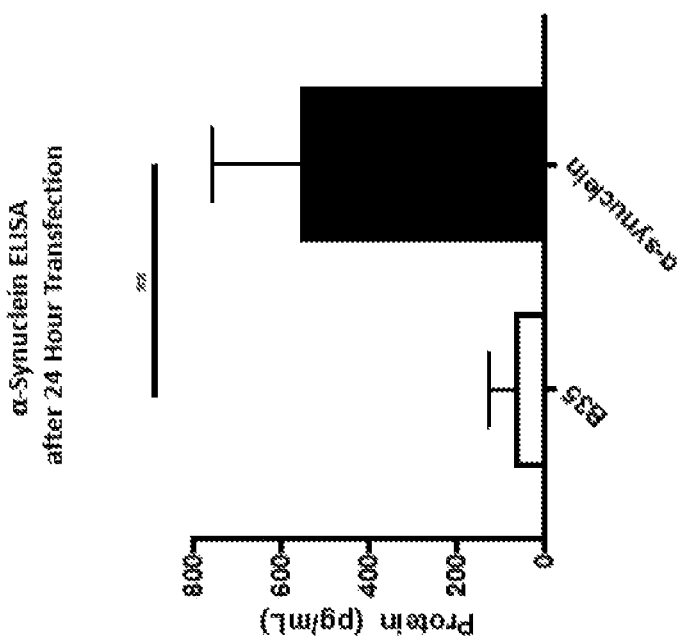
FIG. 4

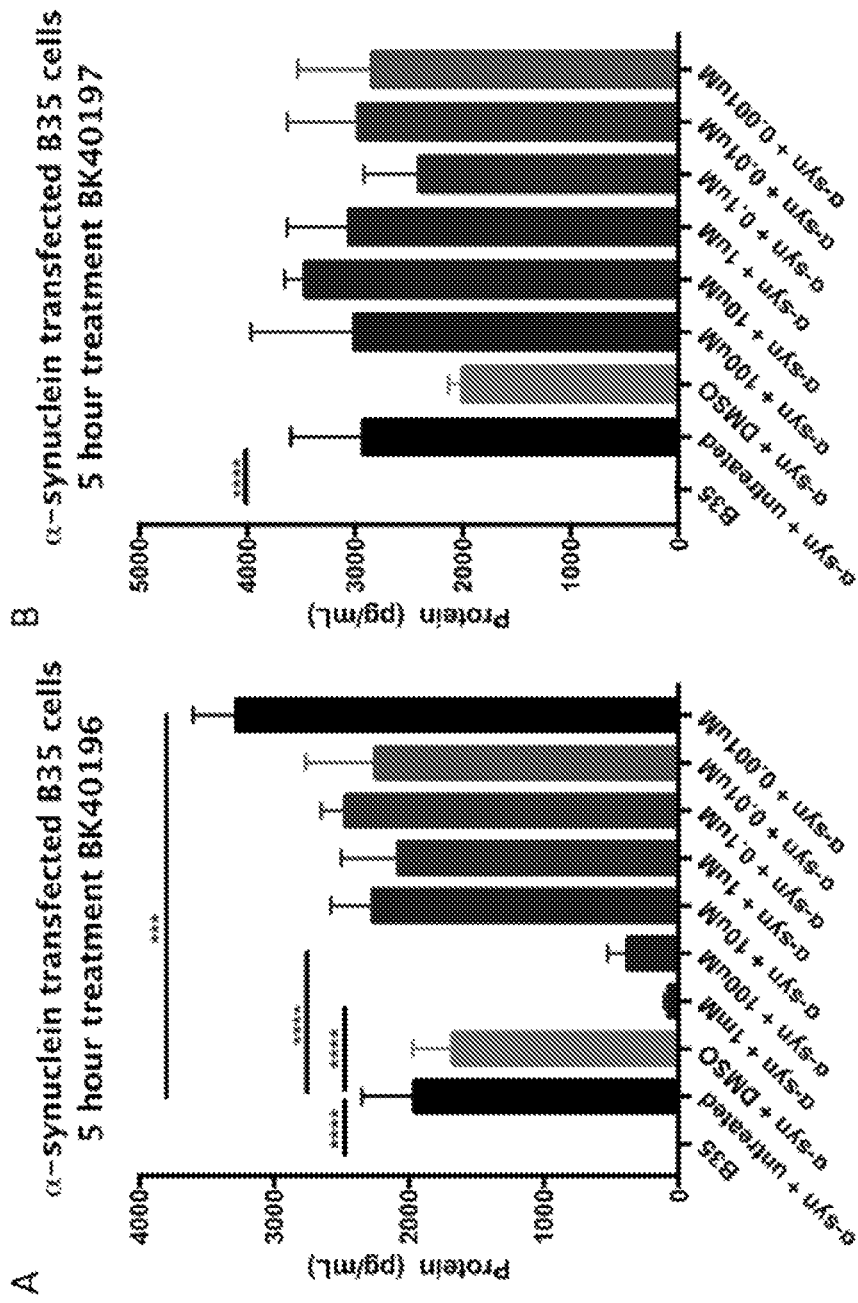
FIGS. 11A-B

A
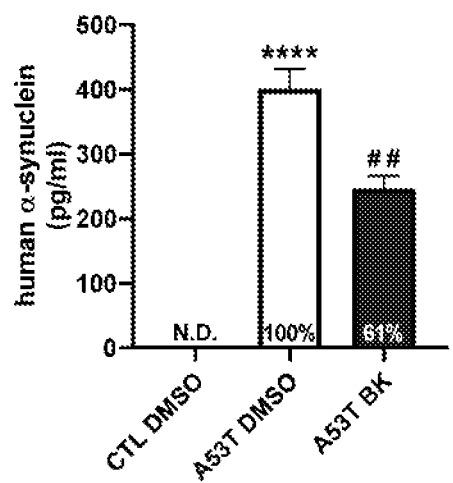
B
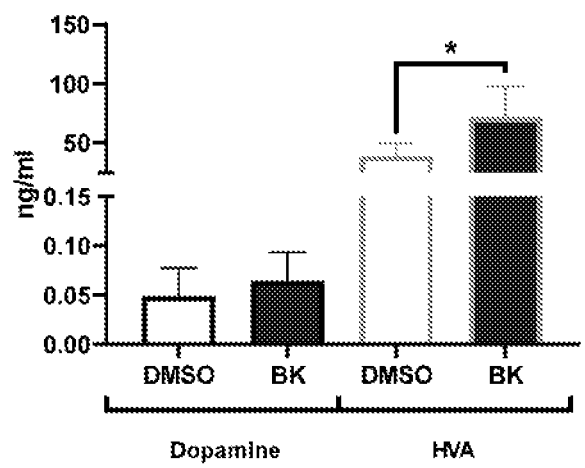
C
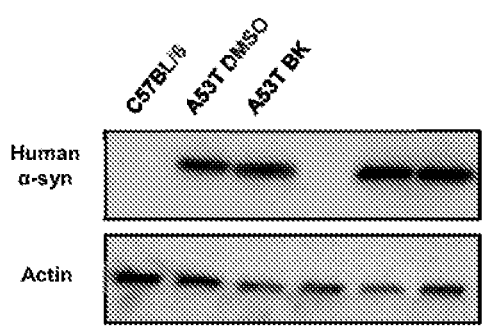
D
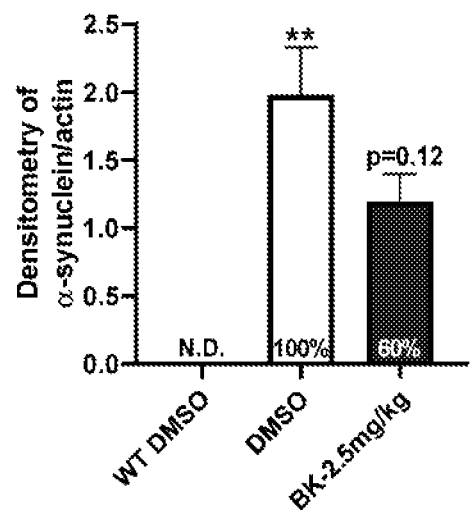
FIGS. 12A-D

COMPOSITIONS AND METHODS FOR TREATING NEURODEGENERATIVE, MYODEGENERATIVE, AND LYSOSOMAL STORAGE DISORDERS

This application claims priority to U.S. Provisional Application No. 62/769,791, filed Nov. 20, 2018, which is hereby incorporated in its entirety by this reference.

BACKGROUND

Neurodegenerative diseases include genetic and sporadic disorders associated with progressive nervous system dysfunction. These diseases are characterized by progressive deterioration of nerve cells or nerve cell function. It has been estimated that one of four Americans will develop a neurodegenerative condition in their lifetimes. Generally, however, the underlying mechanisms causing the conditions are not well understood and few effective treatment options are available for preventing or treating neurodegenerative diseases.

Lysosomal storage disorders represent some of the most devastating of genetic diseases, and the need to develop therapies for these disorders remains largely unmet. Many of these diseases cause damage to the central nervous system (CNS), but the mechanisms underlying such damage are largely unknown. Although the incidence of lysosomal storage disorders is rare (less than about 1:100,000 individuals is affected, lysosomal storage disorders affect mostly children who often die at a young age, many within a few months or years of birth. Many other children die following years of suffering from various symptoms of their particular lysosomal storage disorder.

SUMMARY

Provided herein are compositions and methods for treating or preventing a neurodegenerative disease, a myodegenerative disease, a prion disease or a lysosomal storage disease in a subject. Provided herein are compounds having Formula I

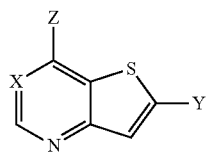

I wherein
X is N or CH;
Y is $C_{6-10}$ aryl unsubstituted or substituted with $R^1$; or $C_{5-10}$ heteroaryl unsubstituted or substituted with $R^1$, or N-methylpiperazinyl:
  $R^1$ is —$(CH_2)_n$—$R^2$, —$(CH_2)$—$C(O)$—$R^2$, or —$O(CH_2)_n$—$R^2$;
  $R^2$ is —H, —CN, halogen, $C_{1-3}$ alkyl, $C_{1-3}$ alkoxy, phenyl, pyridinyl, amino, $C_{1-3}$ alkyl amino, di $C_{1-3}$ alkyl amino, hydroxyl $C_{1-3}$, alkyl amino, carboxy $C_{1-3}$ alkyl amino, $C_{3-6}$ cycloalkyl $C_{1-3}$ alkylamino, pyrrolidinyl, hydroxyl pyrrolidinyl, hydroxyl $C_{1-3}$ alkylpyrolidinyl, carboxypyrolidinyl, piperidinyl, $C_{1-3}$ alkylpiperidinyl, di $C_{1-3}$ alkyl piperidinyl, piperazinyl, $C_{1-3}$ alkylpiperazinyl, $C_{1-4}$ alkoxycarbonylpiperazinyl, or morpholinyl;
Z is heteroaryl, heterocyclyl, or $NR^3R^4$;
  $R^3$ and $R^4$ are independently H, $C_{1-3}$ alkyl, $C_{1-3}$ alkoxy, or unsubstituted phenyl, and
n is an integer selected from 0 to 3,
or an isomer or pharmaceutically acceptable salt thereof.

Also provided is a method of treating or preventing a neurodegenerative disease, a myodegenerative disease or a prion disease in a subject, comprising administering to the subject with the neurodegenerative disease, the myodegenerative disease, or the prion disease or at risk for developing the neurodegenerative disease, the myodegenerative disease or the prion disease an effective amount of a compound having Formula I

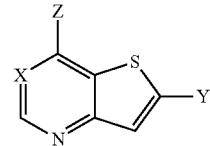

I wherein
X is N or CH;
Y is $C_{6-10}$ aryl unsubstituted or substituted with $R^1$; or $C_{5-10}$ heteroaryl unsubstituted or substituted with $R^1$, or N-methylpiperazinyl:
  $R^1$ is —$(CH_2)_n$—$R^2$, —$(CH2)_n$-$C(O)$—$R^2$, or —$O(CH_2)_n$—$R^2$;
  $R^2$ is —H, —CN, halogen, $C_{1-3}$ alkyl, $C_{1-3}$ alkoxy, phenyl, pyridinyl, amino, $C_{1-3}$ alkyl amino, di $C_{1-3}$ alkyl amino, hydroxyl $C_{1-3}$ alkyl amino, carboxy $C_{1-3}$ alkyl amino, $C_{3-6}$ cycloalkyl $C_{1-3}$ alkylamino, pyrrolidinyl, hydroxyl pyrrolidinyl, hydroxyl $C_{1-3}$ alkylpyrolidinyl, carboxypyrolidinyl, piperidinyl, $C_{1-3}$ alkylpiperidinyl, di $C_{1-3}$ alkyl piperidinyl, piperazinyl, $C_{1-3}$ alkylpiperazinyl, $C_{1-4}$ alkoxycarbonylpiperazinyl, or morpholinyl;
Z is heteroaryl, heterocyclyl or $NR^3R^4$;
  $R^3$ and $R^4$ are independently H, $C_{1-3}$ alkyl, $C_{1-3}$ alkoxy, or unsubstituted phenyl, and
  n is an integer selected from 0 to 3,
or an isomer or pharmaceutically acceptable salt thereof.

Also provided are methods of inhibiting or preventing toxic protein aggregation in a neuron. The methods comprise contacting the neuron with an effective amount of a compound having Formula I:

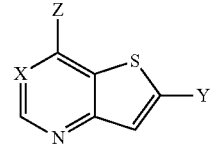

I wherein,
X is N or CH;
Y is $C_{6-10}$ aryl unsubstituted or substituted with $R^1$; or $C_{5-10}$ heteroaryl unsubstituted or substituted with $R^1$, or N-methylpiperazinyl;
  $R^1$ is —$(CH_2)_n$—$R^2$, —$(CH2)_n$-$C(O)$—$R^2$, or —$O(CH_2)_n$—$R^2$;
  $R^2$ is —H, —CN, halogen, $C_{1-3}$ alkyl, $C_{1-3}$ alkoxy, phenyl, pyridinyl, amino, $C_{1-3}$, alkyl amino, di $C_{1-3}$ alkyl amino, hydroxyl $C_{1-3}$ alkyl amino, carboxy $C_{1-3}$ alkyl amino, $C_{3-6}$ cycloalkyl $C_{1-3}$ alkylamino, pyrrolidinyl, hydroxyl pyrrolidinyl, hydroxyl $C_{1-3}$ alkylpyrolidinyl, carboxypyrolidinyl, piperidinyl, $C_{1-3}$ alkylpiperidinyl, di $C_{1-3}$ alkyl piperidinyl piperazinyl, $C_{1-3}$ alkylpiperazinyl, $C_{1-4}$ alkoxycarbonylpiperazinyl, or morpholinyl;

Z is heteroaryl, heterocyclyl, or $NR^3R^4$;

$R^3$ and $R^4$ are independently 14, $C_{1-3}$ alkyl, $C_{1-3}$ alkoxy, or unsubstituted phenyl, and n is an integer selected from 0 to 3, or an isomer or pharmaceutically acceptable salt thereof.

Also provided are methods of treating or preventing a lysosomal storage disorder (LSD) in a subject. The methods comprise administering to the subject having the LSD or at risk of developing the LSD an effective amount of a compound having Formula I:

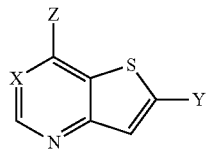

wherein,

X is N or CH;

Y is $C_{6-10}$ aryl unsubstituted or substituted with $R^1$ or $C_{5-10}$ heteroaryl unsubstituted or substituted with $R^1$, or N-methylpiperazinyl;

$R^1$ is $-(CH_2)_n-R^2$, $-(CH2)_n-C(C))-R^2$, or $-O(CH_2)_n-R^2$;

$R^2$ is $-H$, $-CN$, halogen, $C_{1-3}$ alkyl, $C_{1-3}$ alkoxy, phenyl, pyridinyl, amino, $C_{1-3}$ alkyl amino, di $C_{1-3}$ alkyl amino, hydroxyl $C_{1-3}$ alkyl amino, carboxy $C_{1-3}$ alkyl amino, $C_{3-6}$ cycloalkyl $C_{1-3}$ alkylamino, pyrrolidinyl, hydroxyl pyrrolidinyl, hydroxyl $C_{1-3}$ alkylpyrolidinyl, carboxypyrolidinyl, piperidinyl, $C_{1-3}$ alkylpiperidinyl, di $C_{1-3}$ alkyl piperidinyl piperazinyl, $C_{1-3}$ alkylpiperazinyl, $C_{1-4}$ alkoxycarbonylpiperazinyl, or morpholinyl;

Z is heteroaryl, heterocyclyl, or $NR^3R^4$;

$R^3$ and $R^4$ are independently H, $C_{1-3}$, alkyl, $C_{1-3}$ alkoxy, or unsubstituted phenyl, and n is an integer selected from 0 to 3, or an isomer or pharmaceutically acceptable salt thereof.

DESCRIPTION OF THE FIGURES

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 1 (right panel) shows that, after five hours of treatment, there was a stepwise increase in cell viability via decrease in LDH with decreasing concentrations of BK40143.

FIG. 3 shows the level of pTau (181) after 24 hour transfection (left panel, students t-test; unpaired, two-tailed, *p<0.05, *p<0.01) and that BK41043 reduces pTau (181) levels in pTau transfected B35 cells (right panel, n=6, ANOVA; ordinary, one-way, Dunnett's multiple comparisons test, p<0.05, **p<0.0001).

FIG. 4 shows the level of α-synuclein after 24 hour transfection (left panel), and that BK41043 reduces α-synuclein in α-synuclein-transfected B35 cells (right panel). Students t-test: unpaired, two-tailed, *p<0.05, **p<0.0, n=6). Doses of BK40143 ranging from 10 uM-1 mM appear to reduce the level of alpha-synuclein in this cell culture model.

FIG. 11A shows that 1 mM and 100 uM of BK40196 significantly reduced the level of alpha-synuclein in transfected B35 cells.

FIG. 11B shows that BK40197 does not significantly reduce alpha-synuclein levels in transfected B35 cells.

FIGS. 12A-D shows that BK40143 significantly reduces alpha-synuclein in A53T mice. Male and female 12-month old A53T mice were treated i.p. with 2.5 mg/kg of BK40143 for 21 consecutive days. FIG. 12A is an E ISA for human alpha-synuclein show a significant 39% reduction in the level of alpha-synuclein in BK40143 treated animals compared to DMSO treated control A53T mice. $C_{57}BL6J$ mice were used as controls and show no detectable (N.D.) human alpha-synuclein. FIG. 12B shows that BK40143 increases the overall level of dopamine (30%). BK40143 did increase the level of the dopamine metabolite, homovanillic acid (HVA), in A53T mice indicating more dopamine turnover which may result in better dopamine neurotransmission.

FIGS. 12C and 12D) are immunoblots for alpha-synuclein which mirrored the 40% reduction in alpha-synuclein seen in the ELISA.

FIG. 14A, an immunoblot probing for activated (phosphorylated) DDR1 demonstrates that 1.25 and 2.5 but not 5 mg/kg of BK40143 deactivated DDR1. FIG. 14B, an immunoblot probing for activated Src, demonstrates that BK40143 did not engage this tyrosine kinase. FIG. 14C, an immunoblot probing for activated Ab1, demonstrates that BK40143 did not engage this tyrosine kinase. FIG. 14D, an immunoblot probing for phosphorylated Tau (AT8), shows that all three doses of BK40143 reduced the levels of phosphorylated tau by 41-49% percent in the same mice, indicating that DDR inhibition is concurrent with pTau reduction. FIG. 14E is an ELISA for phosphorylated Tau (AT181) showing that 2.5 mg/kg of BK40143 significantly reduced phosphorylated Tau.

FIG. 15A is an immunoblot for aggregating extracellular amyloid-beta (6E10) which demonstrates that 1.25 and 2.5 mg/kg of BK40143 significantly reduced amyloid-beta plaques. FIG. 15B is an immunoblot probing for phosphorylated DDR1 which demonstrates that 1.25 and 2.5 mg/kg of BK40143 deactivated DDR1 by 40% and 31%, respectively. FIG. 15C, probing for activated (phosphorylated Ab1 (245), demonstrates that BK40143 did not engage Ab1. FIGS. 15D and 15E. 1.25 and 2.5 mg/kg BK40143 respectively, significantly reduced soluble human amyloid-beta via ELSA but did not significantly reduce the insoluble amyloid-beta. FIG. 15F shows that 2.5 mg/kg of BK40143 significantly reduced human phosphorylated tau (Ser396) by over 80%.

DETAILED DESCRIPTION

Figure 1:
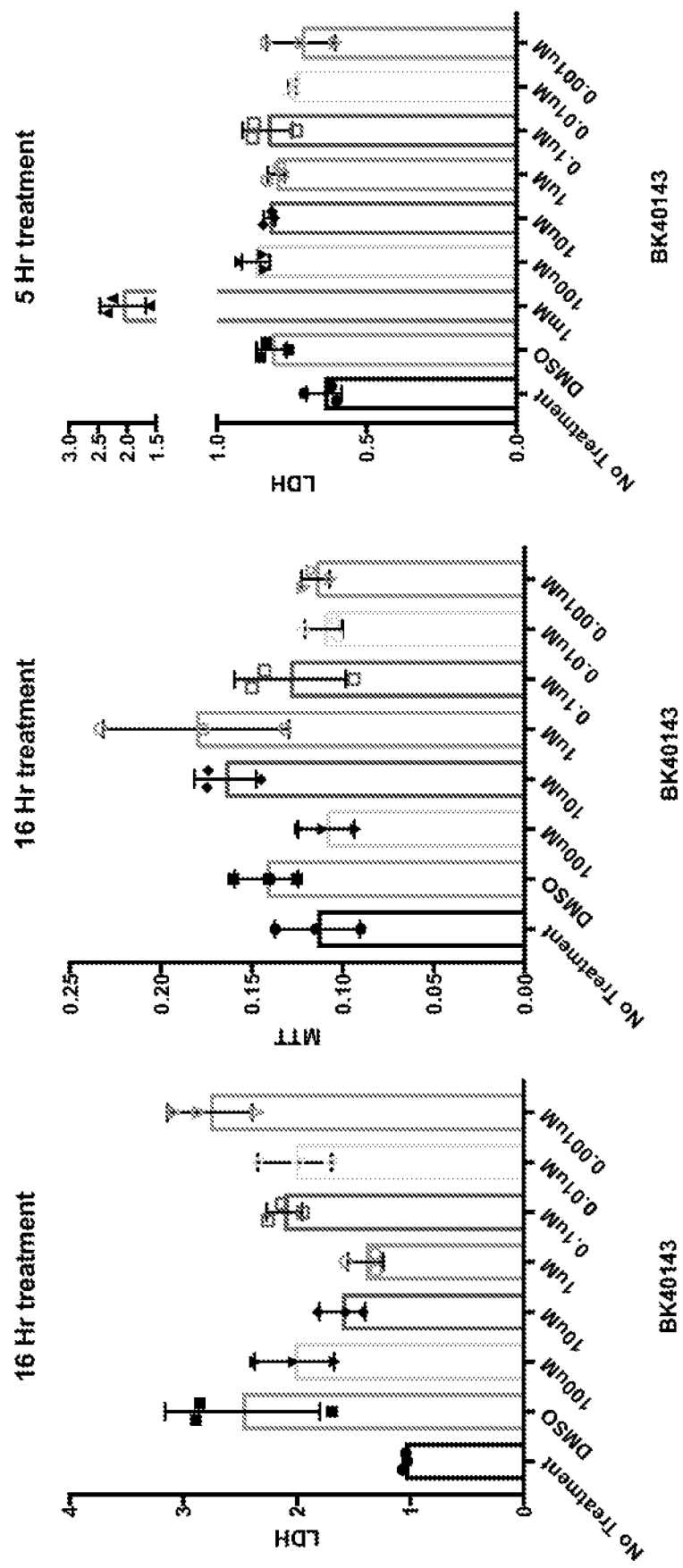
FIG. 1 (left panel and middle panel) shows that, after 16 hours of treatment, neuroprotective effects were observed in B35 cells treated with of 1 µM BK40143, as evidenced by the decrease in lactate dehydrogenase (LDH) and the increase in (3-[4,5-dimethylthiazol-2-yl]-2,5-diphenyl-tetrazolium bromide (MTT), respectively, as compared to control.

Provided herein are compositions and methods for treating or preventing a neurodegenerative disease, a myodegenerative disease, a prion disease or a lysosomal storage disease in a subject.

Compounds

In some examples, a class of compounds described herein includes compounds represented by Formula I:

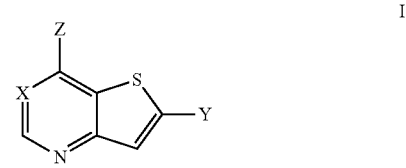

or an isomer or pharmaceutically acceptable salt thereof.

In Formula I, X is N or CH.

Also, in Formula I, Y is $C_{6-10}$ aryl unsubstituted or substituted with $R^1$; or $C_{5-10}$ heteroaryl unsubstituted or substituted with $R^1$, or N-methylpiperazinyl;

Also, in Formula I, $R^1$ is —$(CH_2)_n$—$R^2$, —$(CH2)_n$-C(O)—$R^2$, or —$O(CH_2)_n$—$R^2$;

Additionally, in Formula I, $R^2$ is —H, —CN, halogen, $C_{1-3}$ alkyl, $C_{1-3}$ alkoxy, phenyl, pyridinyl, amino, $C_{1-3}$ alkyl amino, di $C_{1-3}$ alkyl amino, hydroxyl $C_{1-3}$ alkyl amino, carboxy $C_{1-3}$ alkyl amino, $C_{3-6}$ cycloalkyl $C_{1-3}$ alkylamino, pyrrolidinyl, hydroxyl pyrrolidinyl, hydroxyl $C_{1-3}$ alkylpyrolidinyl, carboxypyrolidinyl, piperidinyl, $C_{1-3}$ alkylpiperidinyl, di $C_{1-3}$ alkyl piperidinyl, piperazinyl, $C_{1-3}$ alkylpiperazinyl, $C_{1-4}$ alkoxycarbonylpiperazinyl, or morpholinyl;

Z is heteroaryl, heterocyclyl, or $NR^3R^4$;

Also, in Formula I, $R^3$ and $R^4$ are independently selected from H, $C_{1-3}$ alkyl, $C_{1-3}$ alkoxy, or unsubstituted phenyl, and n is an integer selected from 0 to 3.

In some examples of Formula I, Y is benzyl substituted with $R^1$:

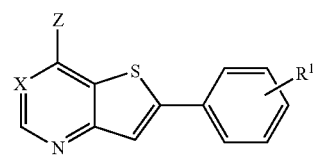

In some examples of Formula I, Y is benzyl substituted with $R^1$ in the meta position:

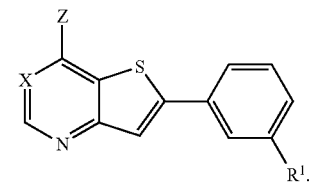

In some examples of Formula I, Z is $NR^3R^4$, $R^3$ is benzyl or H, $R^4$ is benzyl or 11, and Y is benzyl substituted with $R^1$;

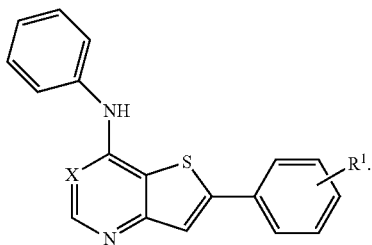

In some examples of Formula I, Z is NR³R⁴, R³ is benzyl or H, R⁴ is benzyl or 1H, and Y is benzyl substituted with R in the meta position:

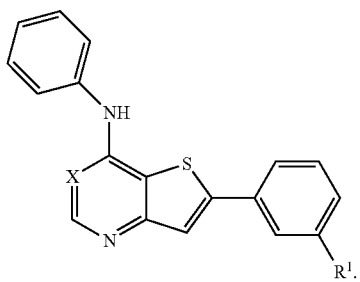

In some examples of Formula I, Z is morpholinyl and Y is benzyl substituted with R¹:

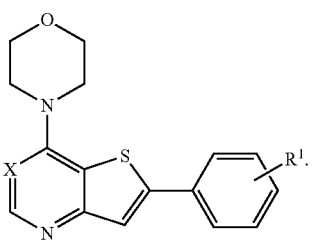

In some examples of Formula I, Z is morpholinyl and Y is benzyl substituted with R¹ in the meta position:

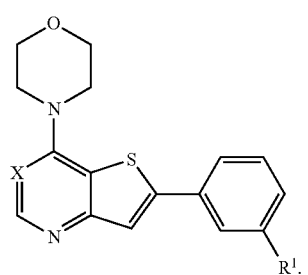

A compound of Formula I is Compound 1 (BK40197):

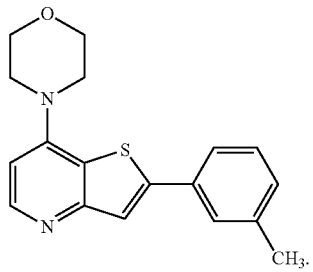

4-(2-(m-tolyl)thieno[3,2-b]pyridin-7-yl)morpholine

Another compound of Formula I is Compound 2 (BK40193):

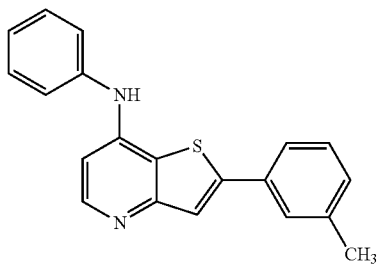

N-phenyl-2-(m-tolyl)thieno[3,2-b]pyridin-7-amine in some examples of Formula I, the compound does not comprise one or more halogen atoms. In some examples of Formula I, Y is 2-m-toluyl. In some examples of Formula I, Z is heterocyclyl. In some examples of Formula I, Z is morpholin-1-yl. In some examples of Formula I, R³ is H and R⁴ is unsubstituted phenyl.

As used herein, the terms alkyl, alkenyl, and alkynyl include straight- and branched-chain monovalent substituents. Examples include methyl, ethyl, isobutyl, 3-butynyl and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_2$-$C_4$ alkyl, $C_2$-$C_4$ alkenyl, and $C_2$-$C_4$ alkynyl.

The term alkoxy as used herein is an alkyl group bound through a single, terminal ether linkage. The term hydroxy as used herein is represented by the formula —OH.

The terms amine or amino as used herein are represented by the formula NR³R⁴, where R³ and R⁴ can each be substitution group as described herein, such as hydrogen, an alkyl, a cycloalkyl, a halogenated alkyl, alkenyl, or alkynyl group described above.

The alkoxy, amino, alkyl, alkenyl, alkynyl, or carbonyl molecules used herein can be substituted or unsubstituted. As used herein, the term substituted includes the addition of an alkoxy, amino, alkyl, alkenyl, alkynyl, or carbonyl group to a position attached to the main chain of the alkoxy, amino, alkyl, alkenyl, alkynyl, or carbonyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term unsubstituted indicates the alkoxy, amino, alkyl, alkenyl, alkynyl, or carbonyl has a full complement of hydrogens, i.e., commensurate with its saturation level, with no substitutions, e.g., linear decane ($—(CH_2)_9—CH_3$).

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$, heteroalkyl, $C_2$-$C_6$ heteroalkenyl, $C_1$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl. $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

Optionally, the compounds having Formula I are tyrosine kinase inhibitors that inhibit one or more receptor tyrosine kinases selected from the group consisting of Abl, PDGFRα, PDGFRβ, DDR 1, DDR2, cKIT, arginase II, Src, Fyn, VEGFR and Zac. In some examples, the compound having Formula I selectively inhibits Abl, PDGFRα, PDGFRβ, DDR1, DDR2, cKIT, arginase II, Src, Fyn or VEGR or Zac. In some examples, the compound having Formula I inhibits DDR 1 and/or DDR2.

As used herein, the term pharmaceutically acceptable salt refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds provided herein, for example, pharmaceutically acceptable salts of nilotinib, bosutinib pazopanib and a compound of Formula I, include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, trifluoroacetic acid, undecanoate, valerate salts, and the like.

The compounds described herein can be prepared in a variety of ways. The compounds can be synthesized using various synthetic methods, including those provided in the Examples. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear-magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Any of the compounds described herein can be modified to enhance blood-brain barrier permeability. Optionally, one or more of the compounds described herein can be administered with an agent that enhances the blood brain barrier permeability of the compound(s).

Methods for Treating or Preventing Neurodegenerative Diseases, Myodegenerative Diseases or Prion Diseases Provided herein are methods of treating or preventing a neurodegenerative disease, a myodegenerative disease or a prion disease. The neurodegenerative disease or disorder can be a neurodegenerative disease of the central nervous system. These include, but are not limited to, amyotrophic lateral sclerosis, Alzheimer's disease, frontotemporal dementia, TDP-43 pathologies, including frontotemporal dementia with TDP-43, frontotemporal dementia linked to chromosome-17, amyloidosis, Pick's disease, Huntington's disease, mild cognitive impairment, an α-synucleinopathy (e.g., Parkinson's disease, Lewy body disease), multiple sclerosis, Glial Cytoplasmic Inclusions, including multiple system atrophy, chronic traumatic encephalopathies, a Tauopathy, progressive supranuclear palsy, and corticobasal degeneration. The neurodegenerative disease can also be a secondary neurodegenerative disease induced by a traumatic brain injury, stroke or an infection, for example, a bacterial or a viral infection (e.g., HIV, Herpes simplex virus (HSV)).

Myodegenerative diseases or disorders include but are not limited to a dystrophy (for example, muscular dystrophy), a myopathy (for example, nemaline myopathy, mulit/minicore myopathy, centronuclear myopathy, mitochondrial myopathy, metabolic myopathy, etc.) or myotonia (for example, myotonia congenita, paramyotonia congenital or myotonic dystrophy).

Prion diseases or disorders include but are not limited to Creutzfeldt-Jakob Disease, Variant Creutzfeldt-Jakob Disease, Gerstmann-Straussler-Scheinker Syndrome, Fatal Familial Insomnia, Kuru, Bovine Spongiform Encephalopathy, Chronic Wasting Disease and Scrapie, to name a few.

The methods comprise administering to the subject with the neurodegenerative disease, myodegenerative disease or prion disease, or at risk of developing the neurodegenerative disease, the myodegenerative disease or the prion disease an effective amount of a compound having Formula I:

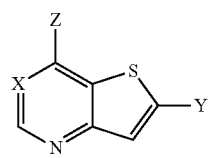

wherein,
X is N or CH;
Y is $C_{6-10}$ aryl unsubstituted or substituted with $R^1$; or $C_{5-10}$ heteroaryl unsubstituted or substituted with R or N-methylpiperazinyl;
$R^1$ is $(CH_2)_n-R^2$, $-(CH2)_n-C(O)-R^2$, or $-O(CH_2)_n-R^2$;
$R^2$ is $-H$, $-CN$, halogen, $C_{1-3}$ alkyl, $C_{1-3}$ alkoxy, phenyl, pyridinyl, amino, $C_{1-3}$ alkyl amino, di $C_{1-3}$ alkyl amino, hydroxyl $C_{1-3}$ alkyl amino, carboxy $C_{1-3}$ alkyl amino, $C_{3-6}$ cycloalkyl $C_{1-3}$ alkylamino, pyrrolidinyl, hydroxyl pyrrolidinyl, hydroxyl $C_{1-3}$ alkylpyrolidinyl, carboxypyrolidinyl, piperidinyl, $C_{1-3}$ alkylpiperidinyl, di $C_{1-3}$ alkyl piperidinyl, piperazinyl, $C_{1-3}$ alkylpiperazinyl, $C_{1-4}$ alkoxycarbonylpiperazinyl, or morpholinyl;

Z is heteroaryl, heterocyclyl, or $NR^3R^4$;

$R^3$ and $R^4$ are independently H, $C_{1-3}$ alkyl, $C_{1-3}$ alkoxy, or unsubstituted phenyl, and n is an integer selected from 0 to 3, or an isomer or pharmaceutically acceptable salt thereof.

In some methods, the compound having Formula I does not comprise one or more halogen atoms. In some methods, Y is 2-m-toluyl in the compound having Formula I. In some methods, Z is heterocyclyl in the compound having Formula L In some methods, Z is morpholin-1-yl in the compound having Formula I. In some methods, $R^3$ is H and $R^4$ is unsubstituted phenyl in the compound having Formula I.

In some methods, a compound having Formula I, wherein Y is benzyl substituted with $R^1$ is administered to the subject:

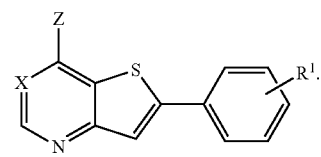

In some methods, a compound having Formula I, wherein Y is benzyl substituted with $R^1$ in the meta position, is administered to the subject:

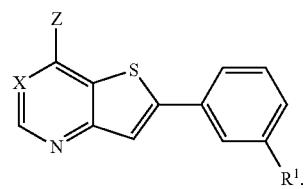

In some methods, a compound having Formula I, wherein Z is $NR^3R^4$, $R^3$ is benzyl or H, $R^4$ is benzyl or H, and Y is benzyl substituted with $R^1$ is administered to the subject:

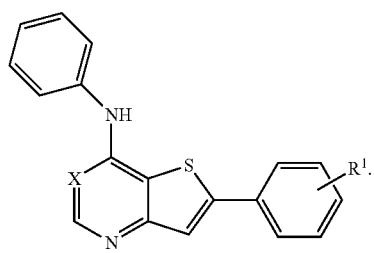

In some methods, a compound of Formula I, wherein Z is $NR^3R^4$, $R^3$ is benzyl or H, $R^4$ is benzyl or H, and Y is benzyl substituted with $R^1$ in the meta position, is administered to the subject:

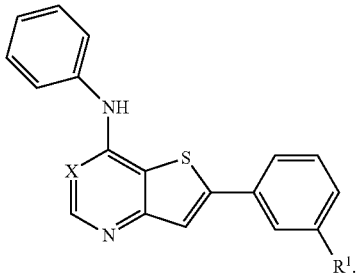

In some methods, a compound of Formula I, herein Z is morpholinyl and Y is benzyl substituted with $R^1$ is administered to the subject:

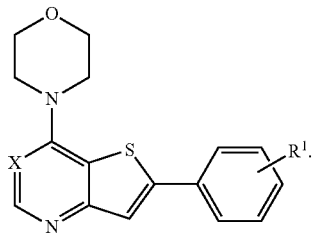

In some methods, a compound of Formula I, wherein Z is morpholinyl and Y is benzyl substituted with $R^1$ in the meta position is administered to the subject:

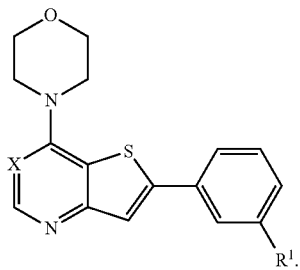

Examples of Formula I that can be used in any of the methods described herein include the following compounds:

Compound 1 (BK40197)

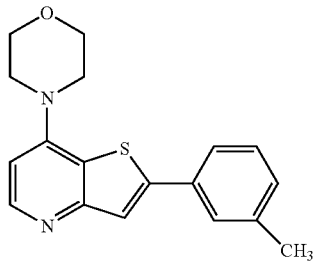

Compound 2 (BK40143)

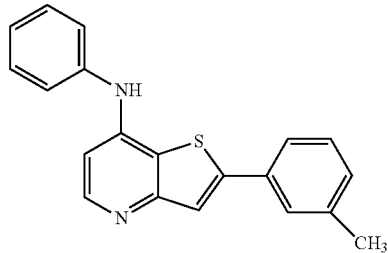

The methods provided herein optionally include selecting a subject with a neurodegenerative disease, a myodegenerative disease or a prion disease or at risk for developing a neurodegenerative disease, a myodegenerative disease or a prion disease. One of skill in the art knows how to diagnose a subject with or at risk of developing a neurodegenerative disease, a myodegenerative disease or a prion disease. For example, one or more of the follow tests can be used; a genetic test (e.g., identification of a mutation in TDP-43 gene) or familial analysis (e.g., family history), central nervous system imaging (e.g., magnetic resonance imaging and positron emission tomography), electroencephalography, clinical or behavioral tests (e.g., assessments of muscle weakness, tremor, gait, or memory), or laboratory tests.

The method optionally further includes administering a second therapeutic agent to the subject. The second therapeutic agent is selected from the group consisting of levadopa, a dopamine agonist, an anticholinergic agent, a cholinergic agent (e.g., 5-hydroxytryptamine (5-HT) inhibitors), a monoamine oxidase inhibitor; a COMT inhibitor, donepezil, memantine, risperidone, amantadine, rivastigmine, an NMDA antagonist, an acetylcholinesterase inhibitor, a cholinesterase inhibitor, riluzole, an anti-psychotic agent, an antidepressant, a glucocorticoid (for example, prednisone), a tyrosine kinase inhibitor (e.g., nilotinib, bosutinib, imatinib, pazopanib, etc.), and tetrabenazine. The second therapeutic agent or therapy can be administered to the subject prior to, simultaneously with, or subsequent to administration of the compound having Formula L.

In the methods where a tyrosine kinase inhibitor is administered as a second therapeutic agent, the tyrosine kinase inhibitor can be a tyrosine kinase inhibitor that does not inhibit a tyrosine kinase receptor that is inhibited by the compound of Formula I or has decreased selectivity for a tyrosine kinase receptor, as compared to a compound of Formula I.

Also provided herein is a method of inhibiting or preventing toxic protein aggregation in a neuron and/or rescuing a neuron from degeneration. As used herein, references to inhibiting, decreasing or reducing include a change of 10%, 20%, 30%, 40%, 50%, 60%, 70%, 80%, 90% or greater as compared to a control level.

The method includes contacting the neuron with an effective amount of a compound of Formula I. Optionally, the compound having Formula I is Compound 1 or Compound 2. The toxic protein aggregate optionally comprises one or more of an amyloidogenic protein, alpha-synuclein, tau, or TDP-43. By amyloidogenic protein is meant a peptide, polypeptide, or protein that has the ability to aggregate. An example of an amyloidogenic protein is β-amyloid. The contacting is performed in vivo or in vitro. The in viva method is useful in treating a subject with or at risk of developing toxic protein aggregates and comprises administering the compound of Formula I to the subject as described below. The in vitro method is useful, for example, in treating neural cells prior to transplantation. In such case, the compound of Formula I is generally added to a culture medium. Optionally, the target neurons are contacted with a second therapeutic agent as described above.

Methods for Treating or Preventing Lysosomal Storage Disorders

Also provided are methods for treating or preventing a LSD in a subject. The methods comprise administering to the subject with the LSD or at risk of developing the LSD an effective amount of a compound having Formula I:

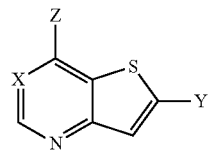

I wherein,

X is N or CH;

Y is $C_{6-10}$ aryl unsubstituted or substituted with $R^1$; or $C_{5-10}$ heteroaryl unsubstituted or substituted with $R^1$, or N-methylpiperazinyl:

$R^1$ is $(CH_2)_n-R^2$, $-(CH2)_n-C(O)-R^2$, or $-(CH_2)_n-R^2$;

$R^2$ is H, —CN, halogen, $C_{1-3}$ alkyl, $C_{1-3}$ alkoxy, phenyl, pyridinyl, amino. $C_{1-3}$ alkyl amino, di $C_{1-3}$ alkyl amino, hydroxyl $C_{1-3}$ alkyl amino, carboxy $C_{1-3}$ alkyl amino, $C_{3-6}$ cycloalkyl $C_{1-3}$ alkylamino, pyrrolidinyl, hydroxyl pyrrolidinyl, hydroxyl $C_{1-3}$ alkylpyrolidinyl, carboxypyrolidinyl, piperidinyl, $C_{1-3}$ alkylpiperidinyl, di $C_{1-3}$ alkyl piperidinyl, piperazinyl, $C_{1-3}$ alkylpiperazinyl, $C_{1-4}$ alkoxycarbonylpiperazinyl, or morpholinyl;

Z is heteroaryl, heterocyclyl, or $NR^3R^4$;

$R^3$ and $R^4$ are independently H, $C_{1-3}$ alkyl, $C_{1-3}$ alkoxy, or unsubstituted phenyl, and n is an integer selected from 0 to 3, or an isomer or pharmaceutically acceptable salt thereof.

In some methods, the compound having Formula I does not comprise one or more halogen atoms. In some methods, Y is 2-m-toluyl in the compound having Formula I. In some methods Z is heterocyclyl in the compound having Formula L In some methods, Z is morpholin-1-yl in the compound having Formula I. In some methods, $R^3$ is H and $R^4$ is unsubstituted phenyl in the compound having Formula L In some methods, a compound having Formula I, wherein Y is benzyl substituted with $R^1$ is administered to the subject:

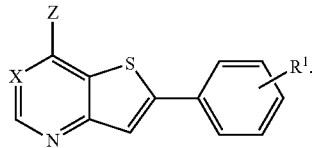

In some methods, a compound having Formula I, wherein Y is benzyl substituted with $R^1$ in the meta position, is administered to the subject:

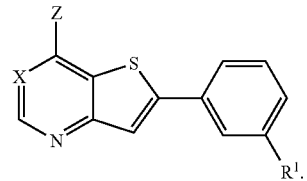

In some methods, a compound having Formula I, wherein Z is $NR^3R^4$, $R^3$ is benzyl or H, $R^4$ is benzyl or H, and Y is benzyl substituted with $R^1$ is administered to the subject:

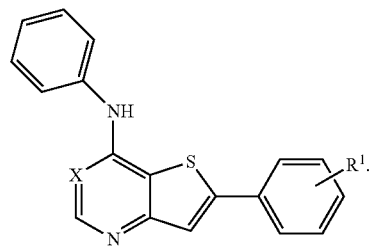

In some methods, a compound of Formula I, wherein Z is $NR^3R^4$, $R^3$ is benzyl or H, $R^4$ is benzyl or H, and Y is benzyl substituted with R in the meta position, is administered to the subject:

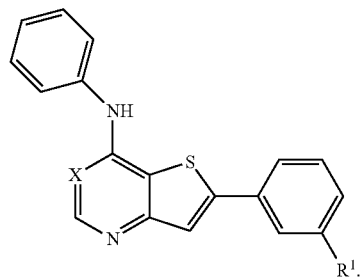

In some methods, a compound of Formula I, herein Z is morpholinyl and Y is benzyl substituted with $R^1$ is administered to the subject:

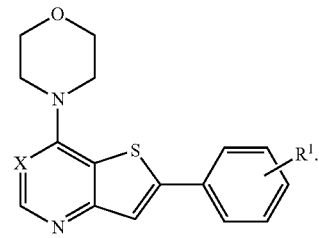

In some methods, a compound of Formula I, wherein Z is morpholinyl and Y is benzyl substituted with R[1] in the meta position is administered to the subject:

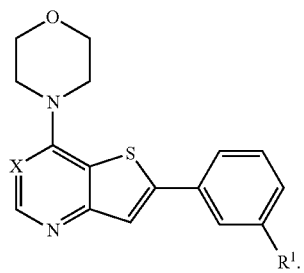

Examples of Formula I that can be used to treat or prevent LSD include the following compounds:

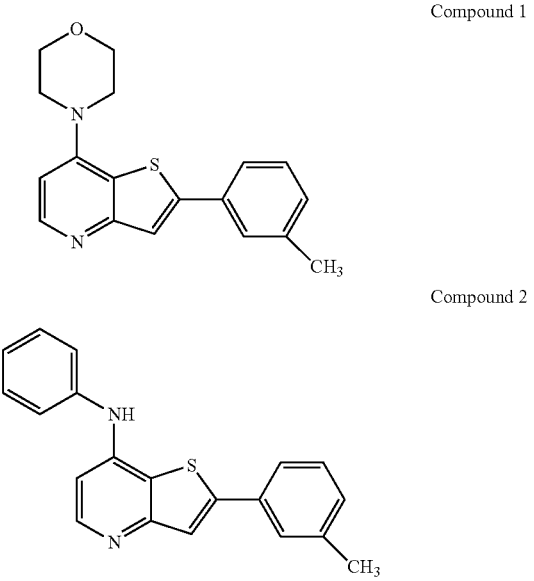

Compound 1

Compound 2

Optionally, the compound of Formula I inhibits one or more receptor tyrosine kinases selected from the group consisting of Ab1, PDGFRα, PDGFRβ, DDR 1, DDR2, cKIT, arginase II, Src, Fyn, VEGFR and Zac. In some examples, the compound of Formula I selectively inhibits Ab1, PDGFRα, PDGFRβ, DDR 1, DDR2, cKIT, arginase II, Src, Fyn or VEGR or Zac. In some examples, the compound having Formula I inhibits DDR 1 and/or DDR2. For example, and not to be limiting, Compound 1 or Compound 2 can be used to inhibit DDR1 and/or DDR2.

In another example, the compound having Formula I, for example, Compound 1 or Compound 2 selectively inhibits DDR 1 or DDR2. LSDs are inherited metabolic disorders that result from defects in lysosomal function. In the majority of cases, LSDs are caused by a deficiency of specific enzymes responsible for degradation of lipids and glycoproteins present in lysosomes. In some cases, defective non-enzymatic lysosomal proteins or non-lysosomal proteins involved in lysosomal biogenesis cause LSDs. The progressive lysosomal accumulation of undegraded metabolites results in generalized cell and tissue dysfunction, and, therefore, multi-systemic pathology. LSDs that can be treated or prevented using the methods provided herein include, but are not limited to, Mucopolysaccharidosis Type I (for example, Hurler syndrome, Hurler-Scheie syndrome and Scheie syndrome), Mucopolysaccharidosis Type I (for example, Hunter syndrome), Mucopolysaccharidosis Type III (for example, Sanfillipo syndrome A, Sanfillipo syndrome B, Sanfillipo syndrome C and Sanfillipo syndrome D), Mucopolysaccharidosis Type IV (for example, Morquio syndrome A and Morquio syndrome B), Mucopolysaccharidosis Type VII (for example, Maroteaux-Lamy syndrome), Mucopolysaccharidosis Type VII (for example, Sly syndrome) Mucopolysaccharidosis Type IX (for example, Natowicz syndrome), Pseudo-Hurler polydystrophy, Tay-Sachs, Gaucher disease, Niemann-Pick disease, Fucosidosis, Galactosialidosis, Globoid-cell leukodystrophy, $G_{M1}$ Gangliosidosis, $G_{M2}$ Gangliosidosis, α-Mannosidosis, Metachromatic leukodystrophy and Pompe disease. The LSDs provided herein are examples of diseases or disorders associated with decreased lysosomal clearance.

Also provided are methods of promoting lysosomal clearance in one or more cells of a subject comprising administering to the subject that has a disorder associated with decreased lysosomal clearance an effective amount of a compound having Formula I. Optionally, the compound having Formula I is Compound 1 or Compound 2. As used throughout, lysosomal clearance is a process by which accumulating lipids, proteins, glycoproteins or a combination thereof are metabolized or degraded in the lysosome of one or lore cells in the subject. A decrease in lysosomal clearance means a decrease in degradation of lipids, proteins and/or glycoproteins in the lysosome of one or more cells of the subject as compared to a control, for example as compared to lysosomal clearance in one or more cells of a healthy subject. Any disorder associated with decreased lysosomal clearance can be treated using the methods provided herein, including, but limited to, any of the LSDs set forth throughout. As used herein, references to promoting or increasing include a change of 10%, 20%, 30%, 40%, 50%, 60%, 70%, 80%, 90% 100%, 200%, 400% or greater as compared to a control level. Optionally, promoting lysosomal clearance decreases the amount of a lipid, a protein, a glycoprotein or a combination thereof in existing aggregates in the lysosome of one or more cells in a subject. Optionally, promoting lysosomal clearance inhibits or prevents formation of aggregates comprising a lipid, a protein, a glycoprotein or a combination thereof in the lysosome of one or more cells in a subject. Optionally, promoting lysosomal clearance decreases the amount of time required to degrade or metabolize a lipid, a protein, a glycoprotein or a combination thereof in one or more cells of the subject as compared to a control.

Optionally, in the methods provided herein, the effective amount of a compound having Formula I inhibits or prevents toxic substance aggregation or accumulation in one or more cells of the subject as compared to a control. As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination of the toxic substance in one or more cells of the subject. Optionally, the one or more cells are brain cells, cells in one or more peripheral tissues of the subject, or a combination thereof. Optionally, the brain cells can be neurons and/or glial cells. In the methods provided herein, a toxic substance that can aggregate or accumulate in cells can be one or more of a lipid, a protein or a glycoprotein. The toxic substance(s) can increase cell damage and/or increase cell death in one or more cells of the subject. In the methods provided herein, the toxic substance(s) can be in the lysosome or elsewhere in one or more cells of the subject. For example, and not to be limiting. LSDs characterized by an accumulation of lipids in the cells of a subject include, but are not limited to, sphingolipidoses (including Gaucher's and Niemann-Pick diseases), gangliosidosis (including Tay-Sachs disease), leukodystrophies; mucopolysaccharidoses (including Hunter syndrome and Hurler disease), glycoprotein storage disorders, mucolipidoses, and glycogen storage disease type II (Pompe disease).

Lipids and glycoproteins that accumulate in sphingolipidoses include sphingomyelin in brain and red blood cells (Nieman Pick Disease); glycoplipids, including ceramide trihexoside, in brain heart and kidney (Fabry disease); galactocerebroside in oligondendrocytes (Krabbe disease); glucocerebrosides in red blood cells, spleen and liver (Gaucher disease); GM2 gangliosides in neurons (Tay-Sachs disease) and Sandhoff disease; GM1 gangliosides; and sulfatide compounds in neural tissue (metachromatic leukodystrophy).

Lysosomal storage diseases also include mucopolysaccharidoses (MP) that have a deficiency in one or more lysosomal enzymes, for example, α-L-iduronidate (Hurler disease, Scheie syndrome and Hurler Schei syndome); iduronate sulphate (hunter disease) heparan sulfate (Sanfilipo type A), N-acetyl-αD-glucosamine (Sanfilipo type B), CoA-α-glucosaminide-N-aceteltytranfer (Sanfilipo type C), N-Acetyl-α-D-glucosaminide-6-sulfate (Sanfilipo type D and Morquio syndrome type A), B-galactose (Morquio syndrome type B) and N-acetylegalatosamine (Maroteaus-Lamy disease) but all of these MPs diseases are a result of lysosomal accumulation of heparan sulfate, dermatan sulfate or kerafan sulfate. Glycogen storage diseases (i.e Pompe disease) result from storage of sugars and phosphorylated sugars in the lysosomes.

The methods provided herein optionally include selecting a subject with a LSD. One of skill in the art knows how to diagnose a subject with a LSD. For example, one or more of the following tests can be used: a genetic test (e.g., identification of a mutation associated with a LSD) or familial analysis (e.g., family history, genetic testing of parents), central nervous system imaging (e.g., magnetic resonance imaging and positron emission tomography), clinical or behavioral tests (e.g., assessments to identify mood disorders, aggressiveness and/or cognitive abnormalities), or laboratory tests (e.g., blood and/or urine tests to identify abnormal levels of metabolites or enzymatic deficiencies).

The methods provided herein optionally further include administering an effective amount of a second therapeutic agent or therapy to the subject. The second therapeutic agent or therapy can be administered to the subject prior to, simultaneously with, or subsequent to administration of the compound of Formula I. The second therapeutic agent or therapy is selected from the group consisting of an enzyme, hematopoietic stem cells, a bone marrow transplant, gene therapy or a small molecule. For example, and not to be limiting, LSDs associated with an enzymatic deficiency can be treated with an enzyme to increase the amount of the deficient enzyme in the subject. For example, enzyme replacement therapy (ERT) with a recombinant enzyme, such as imiglucerase (Cerezyme®), velaglucerase alfa (VPRIV®) or taliglucerase alfa (Elelyso®), can be used as a second therapeutic agent to treat Type I Gaucher disease. Small molecules that inhibit glycosylceramide synthase, for example, miglustat and eliglustat, can also be used to treat Type I Gaucher disease. A small molecule that acts as a chaperone to stabilize a defective enzyme produced by the subject or a small molecule that reduces the amount of one or more substrates that would normally be processed by an enzyme in the subject can also be used.

One or more therapeutic agents that reduce the symptoms of a LSD can also be administered. For example, an anti-epileptic such as gabapentin or lamotrigine can be used to prevent seizures in a subject. Antibiotics can be used to treat bacterial infections such as pneumonia. Other agents include, but are not limited to, anti-inflammatory agents (e.g., NSAIDs and anti-inflammatory steroids), and muscle relaxants. Dialysis, physical therapy and surgery are also contemplated herein as therapies to treat a LSD.

In some methods for treating or preventing a LSD, the second therapeutic agent can be a tyrosine kinase inhibitor (e.g., nilotinib, bosutinib, imatinib, pazopanib, etc.). Therefore, in some examples, a tyrosine kinase and a compound of Formula I are administered to the subject. In the methods where a tyrosine kinase is administered as a second therapeutic agent, the tyrosine kinase can be a tyrosine kinase inhibitor that differs in selectivity for one or more receptor tyrosine kinases as compared to the compound of Formula I.

Pharmaceutical Compositions

The term effective amount, as used throughout, is defined as any amount necessary to produce a desired physiologic response, for example, inhibiting or preventing toxic protein aggregation in a neuron or promoting lysosomal clearance.

Exemplary dosage amounts for administration of any compound described herein, for example, a compound of Formula I, include doses from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 50 mg/kg of body weight of active compound per day, about 1 to about 40 mg/kg of body weight of active compound per day, about 1 to about 30 mg/kg of body weight of active compound per day, about 1 to about 30 mg/kg of body weight of active compound per day, about 30 mg/kg of body weight of active compound per day about 20 mg/kg of body weight of active compound per day, about 10 mg/kg of body weight of active compound per day, or about 5 mg/kg of body weight of active compound per day.

Optionally, the dosage is less than about 10 mg/kg and can be less than about 9.5, 9, 8.5, 8, 7.5, 7, 6.5, 6, 5.5, 5, 4.5, 4, 3.5, 3, 2.5, 2, 1.5, 1.25, 1.0, 0.9, 0.8, 0:7, 06, 0.5, 0.4, 0.3, 0.2, 0.1 mg/kg or any dosage in between these amounts. The dosage can range from about 0.1 mg/kg to about 10 mg/kg, from about 0.1 mg/kg to about 9 mg/kg, from about 0.1 mg/kg to about 8 mg/kg, from about 0.1 mg/kg to about 7 mg/kg, from about 0.1 mg/kg to about 6 mg/kg, from about 0.1 mg/kg to about 5 mg/kg, from about 0.1 mg/kg to about 4 mg/kg, from about 0.1 mg/kg to about 3 mg/kg, from about 0.1 mg/kg to about 2 mg/kg, from about 0.1 mg/kg to about 1 mg/kg, or from about 0.1 mg/kg to about 0.5 mg/kg. One of skill in the art would adjust the dosage as described below based on specific characteristics of the inhibitor and the subject receiving it.

The composition can comprise a single unit dose of a compound of Formula I, for example, a single unit dose of about 50 mg/kg or less, 40 mg/kg or less, 30 mg/kg or less, 20 mg/kg or less, 10 mg/kg or less, of about 5 mg/kg or less, of about 2.5 mg/kg or less or about 1.5 mg/kg or less of Compound 1 or Compound 2, or a pharmaceutically acceptable salt thereof.

Packages including one or multiple, single unit doses of a compound having Formula I, for example, multiple, single unit doses of Compound 1 or Compound 2 are also provided. The package can further comprise single or multiple unit doses of one or more second therapeutic agents described herein.

Effective amounts and schedules for administering one or more of the compounds having Formula I described herein can be determined empirically and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, unwanted cell death, and the like. Generally, the dosage will vary with the type of inhibitor, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary and can be administered in one or more dose administrations daily.

The compounds having Formula I and other agents described herein can be provided in a pharmaceutical composition. These include, for example, a pharmaceutical composition comprising a therapeutically effective amount of one or more compounds having Formula I and a pharmaceutical carrier. The term carrier means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject. Such pharmaceutically acceptable carriers include sterile biocompatible pharmaceutical carriers, including, but not limited to, saline, buffered saline, artificial cerebral spinal fluid, dextrose, and water.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012).

Examples of physiologically acceptable carriers include buffers such as phosphate buffers, citrate buffer, and buffers with other organic acids; antioxidants including ascorbic acid: low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, New Jersey), polyethylene glycol (PEG), and PLURONICS™ (BASF; Florham Park, NJ).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

The compounds described herein can be incorporated into pharmaceutical compositions which allow for immediate release or delivery of those compounds to a mammal. The compounds described herein can also be incorporated into pharmaceutical compositions which allow for modified release, for example, delayed release or extended release (for example, sustained release or controlled release) of those compounds to a mammal for a period of several days, several weeks, or a month or more. Such formulations are described, for example, in U.S. Pat. Nos. 5,968,895 and 6,180,608 and are otherwise known in the art. Any pharmaceutically-acceptable, delayed release or sustained-release formulation known in the art is contemplated.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

The compositions are administered in a number of ways depending on whether local or systemic treatment is desired, and on the area to be treated. The compositions are administered via any of several routes of administration, including orally, parenterally, intravenously, intraperitoneally, intracranially, intraspinally, intrathecally, intraventricularly, intramuscularly, subcutaneously, intracavity or transdermally. Pharmaceutical compositions can also be delivered locally to the area in need of treatment, for example by topical application or local injection. Effective doses for any of the administration methods described herein can be extrapolated from dose-response curves derived from in vitro or animal model test systems.

Throughout, treat, treating, and treatment refer to a method of reducing or delaying one or more effects or symptoms of a neurogenerative disease, a myodegenerative disease, a prion disease or a lysosomal storage disease. The subject can be diagnosed with a disease or disorder.

Treatment can also refer to a method of reducing the underlying pathology rather than just the symptoms. The effect of the administration to the subject can have the effect of, but is not limited to, reducing one or more symptoms of the disease, a reduction in the severity of the disease, the complete ablation of the disease, or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

As used throughout, by subject is meant an individual. The subject can be an adult subject or a pediatric subject. Pediatric subjects include subjects ranging in age from birth to eighteen years of age. Thus, pediatric subjects of less than about 10 years of age, five years of age, two years of age, one year of age, six months of age, three months of age, one month of age, one week of age or one day of age are also included as subjects. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Synthesis and Characterization of thieno[3,2-b]pyridine Derivatives

General Information

Commercially available 7-chloro-2-iodothieno[3,2-b]pyridine (1), m-tolylboronic acid (2), aniline (4), n-anisidine (5), morpholine (6), reagents, catalysts and solvents were used as purchased without further purification. NMR spectra were obtained at 400 MHz ($^1$H NMR) and 100 MHz ($^{13}$C NMR) in deuterated solvents. Reaction products were purified by column chromatography on silica gel (particle size 40-63 μm) as described below.

Synthetic Methods and Compound Characterization
Synthesis of thieno[3,2-b]pyridine Compounds 7-10
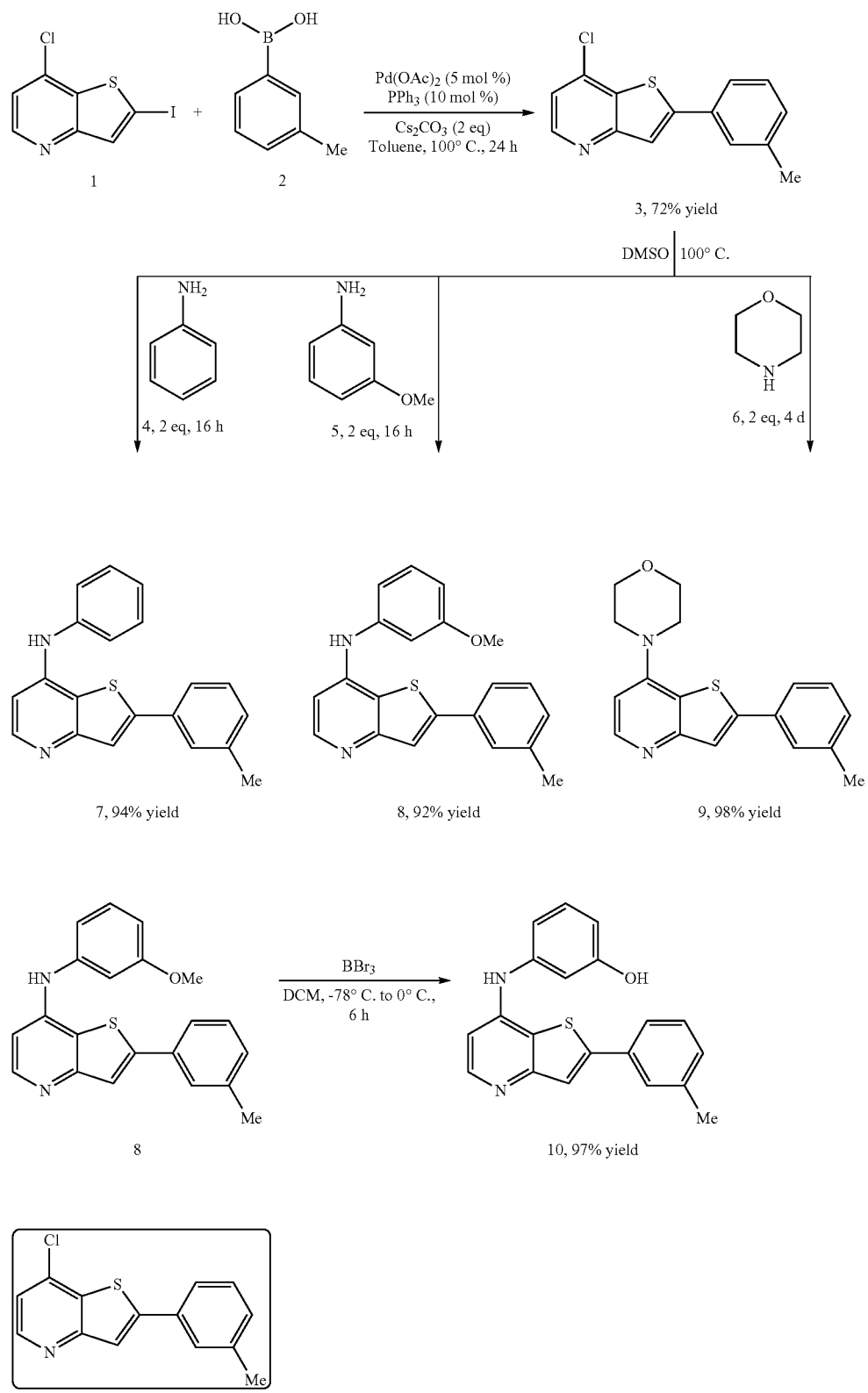

7-Chloro-2-((m-tolyl)thieno[3,2-b]pyridine (3). A mixture of 7-chloro-2-iodothieno[3,2-b]pyridine (1) (500 mg, 1.69 mmol), 3-methylphenylboronic acid (2) (230 mg, 1.69 mmol), palladium(II) acetate (19 mg, 0.084 mmol), triphenylphosphine (44 mg, 0.169 mmol) and cesium carbonate (1.101 g, 3.38 mmol) in 15 mL of toluene was heated at reflux for 24 h. The reaction mixture was cooled to room temperature and partitioned between water and dichloromethane.

The organic layer was washed with saturated aqueous sodium chloride, dried over sodium sulfate, filtered, and concentrated in vacuo. The crude product was purified by flash chromatography on silica gel using hexanes-ethyl acetate (8:2) as mobile phase. Compound 3 was obtained as a colorless solid in 72% yield (315 mg, 1.21 mmol). $R_f$=0.2 (hexanes/EtOAc, 1:1); $^1$H NMR (400 MHz, Chloroform-d) δ=8.54 (d, J=5.1 Hz, 1H), 7.73 (s, 1H), 7.55-7.52 (m, 2H), 7.34 (dd, J=7.8, 7.8 Hz, 1H), 7.23 (m, 1N), 7.21 (d, J=5.1 Hz, 1H), 2.42 (s, 3H); $^{13}$C NMR (100 MHz, Chloroform-d) δ=158.2, 149.6, 148.2, 139.0, 137.6, 133.2, 133.0, 130.4, 129.2, 127.3, 123.8, 120.8, 118.6, 21.5; Anal. Calcd. for $C_{14}H_{10}ClNS$: C, 64.74; H, 3.88; N, 5.39. Found: C, 64.76; H, 4.05; N, 5.28.

General Procedure for the Nucleophilic Aromatic Substitution Reactions

A 5 mL pressure vessel was charged with 7-chloro-2-(m-tolyl)thieno[3,2-b]pyridine (3) (0.3 mmol), the amine (0.6 mmol) and DMSO (1.0 ml). The pressure vessel was then placed in a 100° C. oil bath and stirred for 16 h to 4 days. After full conversion was achieved based on $^1$H NMR analysis, the reaction mixture was extracted with EtOAc and washed with water. The combined organic layers were dried over sodium sulfate and the solvent was removed in vacuo.

The crude product was purified by flash chromatography on silica gel using with hexanes-ethyl acetate as mobile phase as described below.

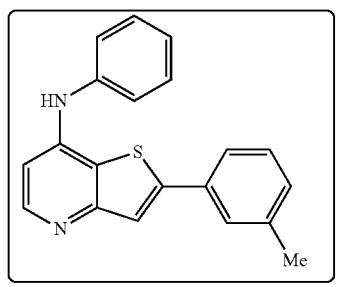

BK-40143

N-Phenyl-2-(m-tolyl)thieno[3,2-b]pyridin-7-amine (7). Compound 7 was obtained as a colorless solid in 94% yield (89 mg, 0.282 mmol) from 7-chloro-2-(r-tolyl)thieno[3,2-b]pyridine (78 mg, 0.3 mmol) and aniline (56 mg, 0.6 mmol) in 1 mL of DMSO after 16 hours at 100° C. by following the general procedure described above. $R_f$=0.2 (hexanes/EtOAc, 1:1); $^1$H NMR (400 MHz, Chloroform-d) δ=8.38 (m, 1H), 7.70 (s, 1H), 7.57-7.50 (m, 2H), 7.43-7.38 (m, 2H), 7.37-7.23 (m, 3H), 7.21-7.17 (m, 2H), 6.90 (m, 1H), 6.15 (s, 1H), 2.43 (s, 3H); $^{13}$C NMR (100 MHz, Chloroform-d) δ=158.5, 148.9, 146.5, 145.9, 139.4, 139.0, 133.7, 129.9, 129.7, 129.6, 129.1, 127.3, 124.8, 123.8, 122.7, 122.5, 121.6, 120.7, 102.6, 21.6; Anal. Calcd. for $C_{20}H_{16}N_2S$: C, 75.92; H, 5.10; N, 8.85. Found: C, 75.71; H, 5.32; N, 9.11.

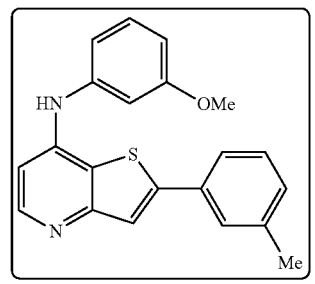

BK40195

N-(3-Methoxyphenyl)-2-(m-tolyl)thieno[3,2-b]pyridin-7-amine (8). Compound 8 was obtained as a colorless solid in 92% yield (95 mg, 0.276 mmol) from 7-chloro-2-(m-tolyl)thieno[3,2-b]pyridine (78 mg, 0.3 mmol) and m-anisidine (74 mg, 0.6 mmol) in 1 mL of DMSO after 16 hours at 100'C by following the general procedure described above. $R_f$=0.2 (hexanes/EtOAc, 2:1); $^1$H NMR (400 MHz, Chloroform-d) δ 8.41 (d, J=: 5.6 Hz, 1H), 7.70 (s, 1H), 7.58-7.51 (in, 21), 7.36-7.29 (m, 2H), 7.21 (d, J=7.9 Hz, 11H), 6.96 (d, J 5.6 Hz, 1H), 6.87 (dd, J=7.9, 2.4 Hz, 1H), 6.83 (dd, J=7.8, 7.7 Hz, 1H), 6.73 (dd, J=7.9, 2.5 Hz, 1H), 6.07 (s, 1H), 3.83 (s, 3H), 2.44 (s, 3H); $^{13}$C NMR (100 MHz, Chloroform-d) δ=160.8, 158.6, 148.9, 146.5, 145.6, 140.7, 139.0, 133.7, 130.5, 130.0, 129.1, 127.3, 123.8, 121.7, 120.9, 114.5, 110.1, 108.1, 103.0, 55.5, 21.6; Anal. Calcd. for $C_{21}H_{18}N_2OS$: C, 72.80; H, 5.24; N, 8.09. Found: C, 72.53; H, 5.61; N, 8.19.

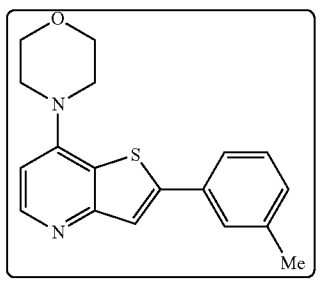

BK40197

4-(2-(m-Tolyl)thieno[3,2-b]pyridin-7-yl)morpholine (9). Compound 9 was obtained as a colorless solid in 98% yield (91 mg, 0.294 mmol) from 7-chloro-2-(m-tolyl)thieno[3,2-b]pyridine (78 mg, 0.3 mmol) and morpholine (52 ng, 0.61 mmol) in 1 mL of DMSO after 4 days at 100° C. by following the general procedure described above. $R_f$=0.2 (hexanes/EtOAc, 1:1); $^1$H NMR (400 MHz, Chloroform-d) δ=8.48 (d, J=5.4 Hz, 1H), 7.69 (s, 11H), 7.59-7.52 (m, 21H), 7.34 (dd, J=7.9, 7.8 Hz, 1H), 7.20 (dd. J=7.9, 2.1 Hz, 1H), 6.64 (d, J=5.4 Hz, 1H), 4.03-3.85 (In, 4H), 3.54-3.39 (m, 4H), 2.43 (s, 3H); $^{13}$C NMR (100 MHz, Chloroform-d) δ=158.8, 153.0, 149.0, 146.6, 139.0, 133.6, 129.9, 129.1, 127.2, 123.7, 123.4, 121.4, 105.9, 66.9, 49.7, 21.6; Anal. Calcd. for $C_{18}H_{18}N_2OS$: C, 69.65; H, 5.85; N, 9.02. Found: C, 69.89; H, 5.72; N, 9.38.

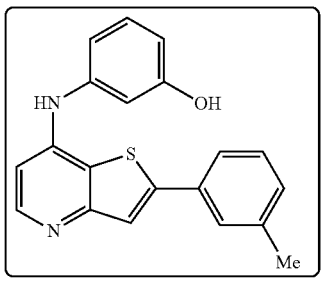

BK40196

3-((2-(m-Tolyl)thieno[3,2-b]pyridin-7-yl)amino)phenol (10). To a solution of N-(3-methoxyphenyl)-2-(m-tolyl)thieno[3,2-h]pyridin-7-amine (8) (69 ng, 0.2 mmol) in dry dichloromethane (3 mL) was added boron tribromide (4 equiv) at −78° C. under inert atmosphere. The mixture was stirred for 4 h and the reaction temperature was allowed to reach 0° C. After quenching with 1M HCl, the crude reaction mixture was extracted with EtOAc and washed with water. The combined organic layers were dried over sodium sulfate and the solvent was removed in vacuo. The crude product was purified by flash chromatography on silica gel using DCM-MeOH (19:1) as mobile phase. Compound 10 was obtained as a colorless solid in 97% yield (64 mg, 0.194 mmol). R/z 0.4 (DCM/MeOH, 9:1); $^1$H NMR (399 MHz, Methanol-$d_4$) δ=8.22 (d, J=6.7 Hz, 1H), 7.70 (s, 1H), 7.65 (s, 1H), 7.61 (dd, J=7.5, 2.1 Hz, 1H), 7.40 (dd, J=7.6, 7.6 Hz, 1H), 7.34-7.31 (m, 2H), 6.93 (d, J=6.7 Hz, 1H), 6.88 (m, 1H), 6.85-6.79 (m, 2H), 2.44 (s, 3H); $^{13}$C NMR (100 MHz, Methanol-$d_4$) δ=160.1, 154.7, 153.5, 149.5, 141.1, 140.7, 139.5, 133.3, 132.4, 131.9, 131.7, 130.5, 128:2, 125.0, 117.4, 115.7, 1.1.4.9, 113.5, 102.7, 21.3; Anal. Calcd. for $C_{20}H_{16}N_2NOS$: C, 72.26; H, 4.85; N, 8.43. Found: C, 72.29; H, 4.97; N, 8.61.

Cell Culture

Rat neuroblastoma B35 cells were grown in Dulbecco's Modified Eagle's Medium (DMEM) with 10% Fetal Bovine Serum (FBS) and 1% penicillin/streptomycin and incubated at 37° C. with 5% $CO_2$. For the experiments, cells were transferred to 12-well plates (Cat. #150628, ThermoFisher, Waltham, MA) and grown to at least 70% confluence. Transient transfection was performed with 3 μg P301 L tau (Cat. #30145, Addgene) cDNA or 3 μg human α-synuclein cDNA using Fugene HD transfection reagent (Cat. #E2311, Promega, Madison WI) for 24 hours. Cells were treated with 1 mM, 100 μM, 10 μM, 1 μM, 0.1 μM, 0.01 μM, and 0.001 μM dissolved in DMSO or an equivalent 5 ul of DMSO for 5 hours. Cell culture media was collected and cells were harvested using sodium-tris, EDTA, NP-40 (STEN) buffer and centrifuged at 10,000×g for 20 minutes at 4'C and supernatant was collected. Cell viability was determined via lactate dehydrogenase assay (Cat. #88954, Thermofisher) and MTT assay (Cat. #V13154, Thermofisher). Protein was extracted by removing culture medium and adding 0.2 ml 1× STEN buffer (50 mM. Tris (pH 7.6), 150 mM NaCl, 2 mM EDTA, 0.2% NP-40, 0.2% BSA, 20 mM. PMSF and protease cocktail inhibitor) to cell layer and incubated on ice for 10 minutes. The bottom of the well was scraped and allowed to incubate on ice for an additional 10 minutes. Cell lysates were collected, stored at −80° C., and used for additional analyses.

Drug Preparation

Compound 1 (BK40197) and Compound 2 (BK40143), with molecular weights of 310.1 and 316.4 g/mol, respectively, were diluted in Dimethyl Sulfoxide (DMSO) to final concentrations of 100 μM, 10 μM, 1 μM, 0.1 μM, 0.01 μM, and 0.001 μM. Drugs were stored at −80° C.

MTT Assay

To measure cell viability, cells were incubated with 500 μL of Dulbecco's Modified Eagle's Medium (DMEM) containing 50 μL of (3-[4,5-dimethylthiazol-2-yl]-2,5-diphenyl-tetrazolium bromide (MTT)) for 4 hours at 37° C. and 5% $CO_2$. The media was aspirated so that 125 uL of media remained. The formazan salts were dissolved in 250 uL of DMSO. Absorbance was read against a blank containing 125 uL of media and MTT, and 250 uL of DMS at 570 nm.

Lactate Dehydrogenase (LDI) Assay

Cellular cytotoxicity was quantitatively measured by assessment of LDH; a cytosolic enzyme that is released from damaged cells into the cellular media, after exposure to the drug 5 hours after initial dosage. The cell culture media was collected, and an aliquot was coupled with a lactate and NAD+. LDH catalyzes the reaction that converts lactate into pyruvate to produce NADH. NADH, in turn, reduces a tetrazolium salt (INT) into a red formazan product. The amount of LDH in the media is proportional to the amount of formazan, which was measured at 490 nm. The absorbance at 680 nm, to measure the background signal from the instrument, was subtracted from the absorbance at 490 nm to calculate the LDH activity.

Cell Culture Transfection and Treatment

To perform transient transfection of α-synuclein into the rat neuroblastoma B35 cells FuGene® HD Transfection Reagent (Promega Corporation, Madison, WI) was used. Cells were grown in 12-well dishes. A mixture containing 12 μg of cDNA, 540 μg of DMEM containing 2% FBS, and 60 μl of FuGene® HD Transfection Reagent was incubated for 10 minutes. The cells were treated with 50 μl of the FuGene® HD Transfection Reagent/DNA mixture for 24 hours. Cells were harvested after transfection, media was aspirated, the cells were treated with 200 ul of Sodium Tris EDTA NP40 (STEN) lysis buffer then scraped off the plate and collected into a 15 ml centrifuge tube.

Mouse Treatment

Experiments were conducted on (a) TgAPP mice which express neuronally derived human APP gene, 770 isoform, containing the Swedish (K670N/M671 L, Dutch E693Q, and Iowa D694N mutations under the control pf the mouse thymus cell antigen 1, theta, Thy1, promotor (Davis et al. "Early-onset and robust cerebral microvascular accumulation of amyloid beta-protein in transgenic mice expressing low levels of a vasculotropic Dutch/Iowa mutant form of amyloid beta-protein precursor," *The Journal of biological chemistry.* 279(19):20296-20306 (2004); (b) rTg4510 mice which express human P301L tau and have the tet-responsive element (TRE or tetO) and mouse prion protein promotor sequences (PrP or Prnp) directing expression of the P301L mutant variant of human four-repeat microtubule-associated protein tau (4R0NTau P301 L) (Santacruz et al. "Tau suppression in a neurodegenerative mouse model improves memory function," Science 309(5733):476-48 (2005); or (c) TgA53T mice which express mutant arginine to threonine (A53T) human α-synuclein under the control of the prion promotor (Giasson et al. "Neuronal alpha-synucleinopathy with severe movement disorder in mice expressing A53T human alpha-synuclein," Neuron 34(4):521-533 (2002). Mice received treatments of daily intraperitoneal (i.p.) injections of BK40143 (BK) (Medicinal Chemistry Program, Georgetown University), Nilotinib (Nilo) (Cat. #S1033, Selleckchem Inc., Houston, TX), Bosutinib (bos) (Cat. #S1014, Selleckchem Inc.), or combined solutions of BK+Nilo, BK+Bos, or Nilo+Bos at 1.25 mg/kg, 2.5 mg/kg, or 5.0 mg/kg dissolved in dimethyl sulfoxide (DMSO) (Cat. #D128-500, Fisher Scientific, Hampton, NH) or an equivalent dose of DMSO only. Treatment periods were either 7 consecutive days or 21 consecutive days as designated in the figure legends.

Xmap

Xmap technology uses magnetic microspheres that are internally coded with two fluorescent dyes. Through precise combinations of these two dyes, multiple proteins were measured within a sample. Each of these spheres is coated with a specific capture antibody. The capture antibody binds to the detection antibody and a reporter molecule, completing the reaction on the surface of the bead. 25 µl of soluble brain tissue lysates, from transgenic Tg4510 mice treated with 5 mg/kg. 2.5 mg/kg and 125 mg/kg of BK40143 or DMSO were incubated overnight (16-20 hours) at room temperature with 25 µl of detection antibody solution, and 25 µl of a mixed bead solution, containing the following analyte: human phospho-tau (181). Following extensive washing of the plate, samples were incubated with 25 µl of Streptavidin-Phycoerythrin was added to each well and incubated for 30 minutes at room temperature. Samples were then washed and suspended in 100 ul of sheath fluid. After resuspension, samples were run on MAGPIX with Xponent software. The Median Fluorescent Intensity (MFI) data was analyzed using a 5-parameter logistic or spline curve-fitting method for calculating analyte concentrations in samples.

Protein Extraction

Brains from treated mice compared with DMSO treated mice were homogenized in STEN lysis buffer [50 mM sodium Tris (pH 7.6), 150 mM NaCl, 2 mM EDTA, 0.2% NP-40, 0.2% BSA, 20 mM PMSF and protease cocktail inhibitor], centrifuged at 10 000 g for 20 min at 48° C. and the supernatant containing the soluble protein fraction was collected. The supernatant was analyzed by Western Blot (WB) on SDS-NuPAGE Bis-Tris gel (Invitrogen, Carlsbad, CA) and ELISA.

Pharmacokinetics Studies

C57BL/6J mice were injected one with i.p. injection of BK. Brain and serum were collected at 2, 4, 6, or 12 h (n=18 per drug, n=3 per dose and time point). Animals injected with vehicle (DMSO) were used for background subtraction. Stock solutions of drug (approximately 1 mg/mL each) were prepared in methanol/dichloromethane (50:50). The serial dilutions for each of the standards were produced for the study separately in methanol/HPLC grade water (50:50). Preparation of the calibration curve standards and quality samples (QC) was performed by mixing the stock solutions in blank samples. Serum and brain samples were stored at −80° C. then thawed to room temperature prior to preparation. The thawed serum samples (20 uL) were transfused to a tube containing 100 uL of water. The 500 uL extraction solvent, acetonitrile/methanol (50:50) was added to the sample. The mixture was vortexed and incubated on ice for 20 min to accelerate protein precipitation. After incubation, the samples were vortexed again and centrifuged at 13,000 rpm for 20 min at 4° C. The supernatant was then collected and transferred to a new tube, dried using speed vac, and reconstituted in 200 uL of methanol/water (50:50). The mixture was spun again at 13,000 rpm for 20 min 200 at 4° C. The supernatant was then collected into a mass spec sample tube cap and run in the mass spectrometer. For the brain, a small section of the thawed brain sample from each animal was transferred to a flat bottom tube. 200 uL of methanol/water (90:10) was added, and the tissue was homogenized. Acetonitrile was then added to the mixture facilitating protein precipitation. The mixture was then incubated on ice for 10 min. After incubation, the samples were vortexed and centrifuged at 13,000 rpm for 20 min at 210 4° C. The supernatant was then collected and transferred to a new tube, dried using speed vac, and reconstituted in 200 uL of methanol/water (50:50). The mixture was centrifuged at 13,000 rpm for 20 min at 4° C. The supernatant was collected into a mass spec sample tube cap and run in the mass spectrometer. The samples were resolved on an Acquity UPLC BEH C18 1.7 µm, 2.1×50 mm column online with a triple quadrupole mass spectrometer (Xevo-TQ-S, Waters Corporation) operating in the multiple reaction monitoring (MRM) mode. The sample cone voltage and collision energies were optimized for both analytes to obtain maximum ion intensity for parent and daughter ions using "IntelliStart" feature of MassLynx software (Waters Corporation). The instrument parameters were optimized to gain maximum specificity and sensitivity of ionization for the parent [m/z=438.25] and daughter ions [m/z=357.33]. Signal intensities from all MRM Q1/Q3 ion pairs for analytes were ranked to ensure selection of the most intense precursor and fragment ion pair for MRM-based quantitation. This approach resulted in the selection of cone voltages and collision energies that maximized the generation of each fragment ion species. An analysis was performed with a six to eight-point calibration curve, the sample queue was randomized and solvent blanks were injected to assess sample carryover. MRM data were processed using Target-Lynx 4.1. The relative quantification values of analytes were determined by calculating the ratio of peak areas of transitions of samples normalized to the peak area of the internal standard.

Tissue Collection and Protein Extraction.

Animals were deeply anesthetized with a mixture of Xylazine and Ketamine (1:8), and 500 ul of whole blood was collected via cardiac puncture, centrifuged at 2000×g to precipitate blood cells and the serum was collected. To wash out the remaining blood from vessels and reduce contamination, animals were perfused with 25 ml of 1× phosphate buffered saline (PBS) for 5 mins. Brains were collected and homogenized in 1.0 ml 1× STEN buffer. Homogenized samples were centrifuged at 12,000×g for 20 min at 4° C. and supernatant (soluble protein fraction) was collected and stored at −80° C. Insoluble protein was extracted after removing the supernatant. The tissue pellet was washed with 1× STEN buffer. The pellet was re-suspended in 750 ul of 70% formic acid and incubated for 30 min at room temperature followed by a centrifugation at 28,000 g at 4° C. for 1 hr. The supernatant was collected as the "insoluble fraction," Samples from the 70% formic acid fraction were stored at −80° C. and neutralized with 1M Tris-base (1:20) immediately before use. Protein levels were quantified using Pierce BCA protein assay (ThermoFisher, 23225) via manufacturer's instructions.

Immunoblot Analysis

Soluble and insoluble proteins extracted from mouse brain lysates were run on SDS NuPAGE Bis-Tris gel (Cat. #NP0301 BOX, Invitrogen) and probed for phosphorylated tau with (1:1000) mouse monoclonal AT180 (Cat #MN1040, ThermoFisher) and (1:1000) mouse monoclonal AT8 (Cat. #MN1020, ThermoFisher), total tau with (1:3000) mouse monoclonal Tau-5 antibody, phosphorylated DDR1 with (1:250) rabbit polyclonal MCK10 (Cat, #PA5-64780, ThermoFisher), ubiquitin with (1:5000) rabbit polyclonal (Cat. #PA3-16717, ThermoFisher), Atg5 with (1:1000) rabbit monoclonal (Cat. #mAb 12994, Cell Signaling, Danvers, MA), Beclin-1 with (1:1000) rabbit monoclonal (Cat. #mAb 3495, Cell Signaling), and Actin with (1:8000) rabbit polyclonal (Cat. #MAB1501R, EMDMillipore, Burlington, MA). Blots were visualized using Super Signal™ West Dura Extended Duration Substrate (Cat. #37071, ThermoFisher) on the Amersham™ Imager 600 (GE Healthcare Life Sciences, Pittsburgh, PA). Western blots were quantified by densitometry using Image J software.

Enzyme Linked Immunosorbent Assay (ELISA)

Human α-synuclein and p-tau ELISA were performed using 50 μl (1 μg/4 μl) of cell lysates detected with 50 μl primary antibody (3 h) and 100 μl anti-rabbit secondary antibody (30 min) at RT. α-Synuclein levels were measured using human specific ELISA (Invitrogen Inc., Carlsbad, CA) according to manufacturer's protocols. Tau was measured using specific tau at serine 396 according to manufacturer's protocol. Each sample was duplicated.

ELISAs for total Tau, $AB_{40}$, and $AB_{42}$ (Millipore Cat #HNABTMAG 60K) were conducted using Milliplexed ELISA. As set forth above, Xmap technology uses magnetic microspheres that are internally coded with two fluorescent dyes. Through precise combinations of these two dyes, multiple proteins are simultaneously measured within a sample. Each of these spheres is coated with a specific capture antibody. The capture antibody hinds to the detection antibody and a reporter molecule, completing the reaction on the surface of the bead. All samples including placebo and resveratrol at baseline and 52 weeks were analyzed in parallel using the same reagents. A total of 25 μl soluble protein was incubated overnight at 4° C. with 25 μl of a mixed bead solution containing total Tau, $AB_{40}$ and $AB_{42}$. After washing, samples were incubated with 25 μl detection antibody solution for 1.5 h at room temperature. Streptavidin-phycoerythrin (25 μl) was added to each well containing the 25 μl of detection antibody solution. Samples were then washed and suspended in 100 μl of sheath fluid. Samples were then run on MAGPIX with Xponent software. The median fluorescent intensity (MFI) data were analyzed using a 5-parameter logistic or spline curve-fitting method for calculating analyte concentrations in samples. Specific p-Tau ser396 (Invitrogen, KHB7031), human Tau thr181 (Invitrogen, KHO063t) and Aβ1-42 (Invitrogen, KHB3442) were performed according to manufacturer's protocol on tissue soluble extracts from midbrain lysates in 1×STEN buffer (see above).

Behavior

Rotarod: mice were placed on an accelerating rod (Cat. #76-0770, Panlab, Harvard Apparatus) equipped with individual timers for each mouse. Mice were tested over 4 trials, 3 training and 1 testing. Mice were trained to stay on the rod at a constant 4 rotations per minute (rpm) for at least 5 minutes, and then the speed will gradually increase to 40 rpm over 300 seconds and the latency to fall was measured.

Open-field: Mice were placed in the open field arena apparatus (25 cm×25 cm) for 60 minutes. Animals were tracked by photocell beams along the arena floor. Data were collected and analyzed for total distance traveled (cm), total time spent moving (sec), and velocity (distance/time) during the 60-minute trial. A center zone was digitally defined in the software as (25 cm×25 cm) in the center of the apparatus and center zone entries, center zone distance travelled (cm), and time spent in center zone (sec) during the 60-minute trial were recorded.

Morris water maze: The water maze apparatus consisted of a 4-foot-diameter pool (San Diego Instruments) filled with water maintained at 25° C. and made opaque with white paint and digitally divided into 4 quadrant zones (ANYMaze software, San Diego Instruments). Extra-maze visual cues were hung on the walls surrounding the pool and a hidden platform (4 inches in diameter) was submerged 1 cm below the surface of the water in the center of the 'platform zone'. Training consisted of three trials per day for four days leading up to a probe trial on the fifth day. The mice were introduced into the pool at one of three entry points, one per non-platform quadrant zone, with every entry point used over the course of the day. The location of the platform remained constant throughout the entire training period. The mice were given 60 sec to locate the platform, and remained on the platform for 10 sec before being removed. Mice that did not locate the platform within 60 see were placed on the platform for 10 sec before removal from the maze. During the probe trial on the fifth day, the platform is removed and the tracking software (ANYMaze) was used to record latency to find the platform, platform quadrant zone, swim speed, and swim path. This training and probe trial paradigm was conducted pre-treatment and post-treatment.

Marble burial test: Marble burying test was performed as previously described [35] with modifications. Briefly, 20 marbles of 15 mm in diameter were spaced by 4 cm in five rows of four marbles each on a surface of gently packed 5-cm-deep corncob bedding in a double-sized rat cage. A mouse was left alone in the cage for 30 minutes. An observer blinded to the treatment counted the number of marbles buried. Any marble buried more than two-thirds of its size was counted. Each mouse was assessed once at pre- and post-treatment and data were reported as average±SEM of the percentage of buried marbles per animal. Kuskal-Wallis tests followed by Wilcoxon post hoc test was used to determine statistical significance of marble burying in mice treated with drug or DMSO.

Statistical Analysis

All statistical analysis was performed using GraphPad Prism, version 8.0 (GraphPad software Inc.). For experiments involving mice, sample size (n) and female:male rations used in each experiment are indicated in the figure legends. For experiments using cell lines the number of independent biological replicates is reported (N). Data are presented as mean±SEM. When comparing averages in two groups, two-tailed Students (test or Welch's t test was performed.

When comparing the averages on multiple groups, one-way analysis of variance (ANOVA) followed by Tukey's multiple comparison post hoc test was performed. Asterisks or the pound symbol denote actual p-value significances (*<0.05; <0.01, *<0.001, ****<0,0001) between groups or within groups and is noted in the individual figure legends.

Results

As shown in FIG. 1 (left panel and middle panel), after 16 hours of treatment, neuroprotective effects were observed in B35 cells treated with 1 μM BK41043, as evidenced by the decrease in LDH and the increase in MTT, respectively, as compared to control. FIG. 1 (right panel) shows that, after five hours of treatment, there was a stepwise increase in cell viability, via decrease in LDH, with decreasing concentrations of BK40143.

Figure 2:
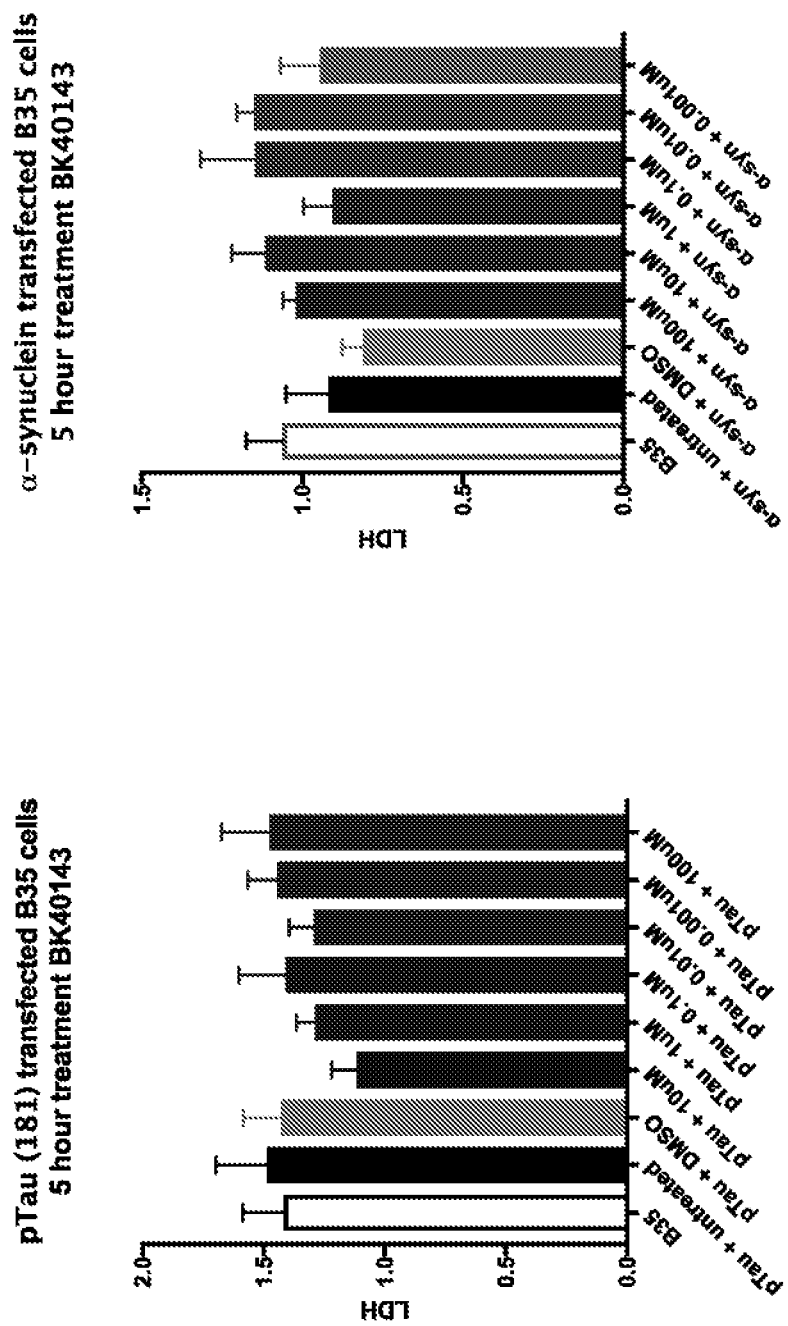
FIG. 2 shows cell viability of B35 cells after 24 hour transfection with pTau (left panel) or α-synuclein (right panel) and five hours of treatment with BK41043. Dehydrogenase (LDH) measured in the media, reflecting cell death, is not different between control and cells expressing tau or α-synuclein, with or without BK40143, indicating that this compound does not result in toxicity or cell death.

FIG. 2 shows cell viability of B35 cells after 24 hour transfection with pTau (left panel) or α-synuclein (right panel) and five hours of treatment with BK41043.

B35 cells were grown in complete media and transfected with cDNA for human-mutant Tau and alpha-synuclein using FuGene HD transfection reagents according to manufacturer's instructions. At 24 hours the transfection had produced significantly higher amounts of phospho-Tau and alpha-synuclein compared to non-transfected cells via ELISA. FIG. 3 shows the level of pTau (181) after 24 hour transfection (left panel) and that BK41043 reduces pTau (181) levels in pTau transfected B35 cells (right panel) back to control levels. This occurred without any change to LDH levels indicating no increased toxicity during the experiment. FIG. 4 shows the level of α-synuclein after 24 hour transfection (left panel) and that BK41043 did not reduce α-synuclein in α-synuclein-transfected B35 cells (right panel).

Figure 5:
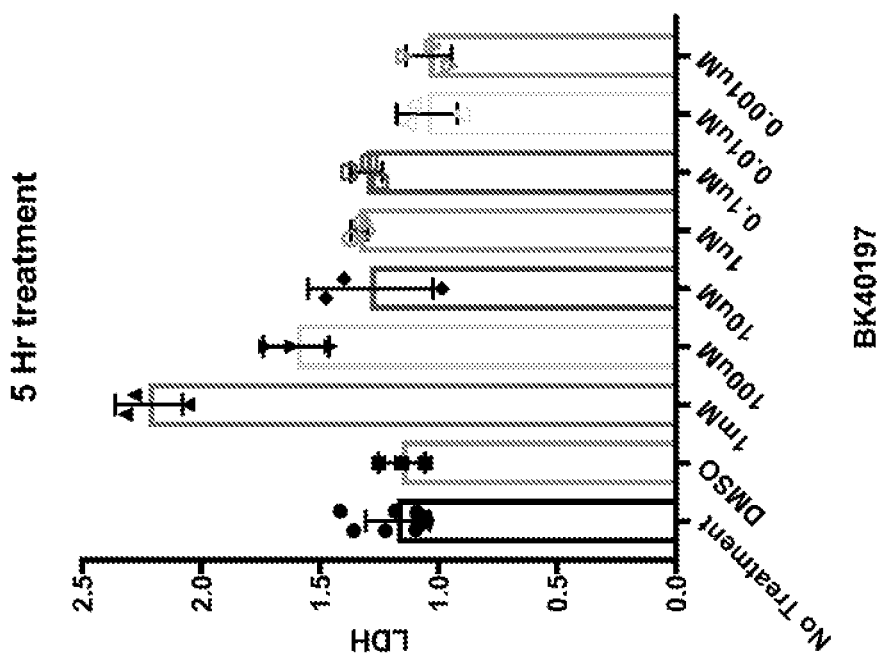
FIG. 5 shows cell viability of B35 cells after five hours of treatment with BK40197.

FIG. 5 shows cell viability of B35 cells after rive hours of treatment with BK40197.

Figure 6:
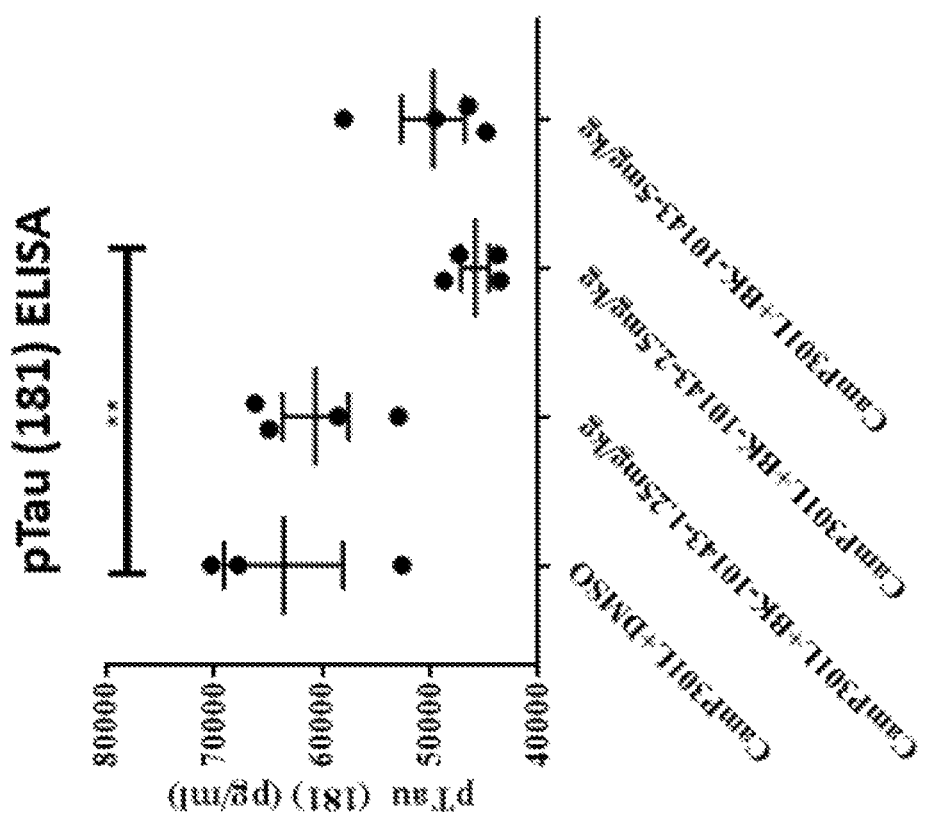
FIG. 6 shows that BK40143 reduces pTau (181) in Tau expressing transgenic mice, after seven days of treatment. The levels of pTau(181) were measured via ELISA. Students t-test: unpaired, two-tailed, Welch's correction, *p<0.05, ***p<0.01

FIG. 6 shows that BK40143 reduces pTau (181) in Tau expressing transgenic mice, after seven days of treatment. The levels of pTau(181) were measured via ELISA.

Figure 7:
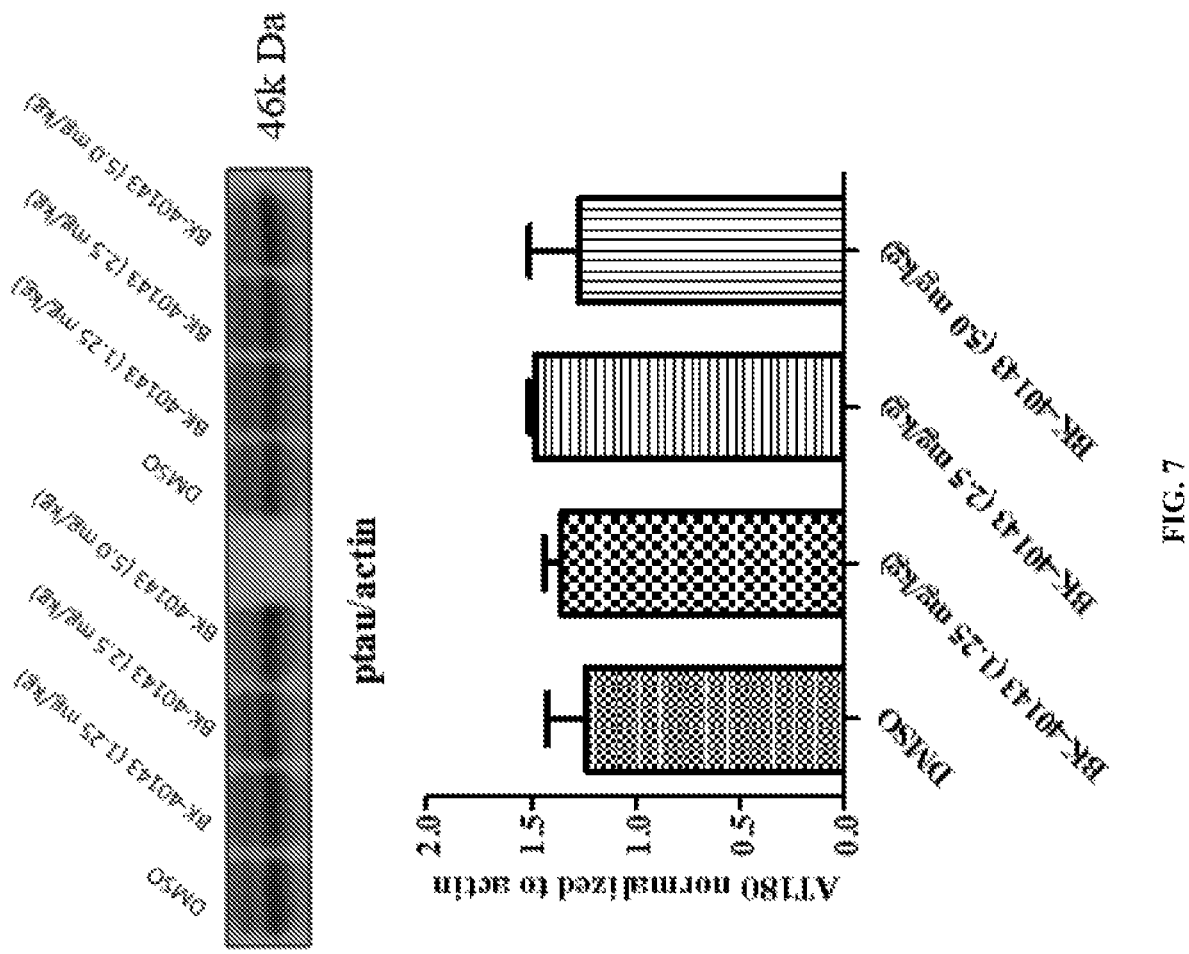
FIG. 7 shows that treatment with BK-40143 (1.25 mg/kg, 2.5 mg/kg or 5.0 mg/kg) did not affect the levels of pTau (231) (AT180) in rTG4510 transgenic mice (n=4), using Western blot analysis.

FIG. 7 shows that treatment with BK-40143 (1.25 mg/kg, 2.5 mg/kg or 5.0 mg/kg) did not affect the levels of pTau (231) (AT180) in transgenic mice.

Figure 8:
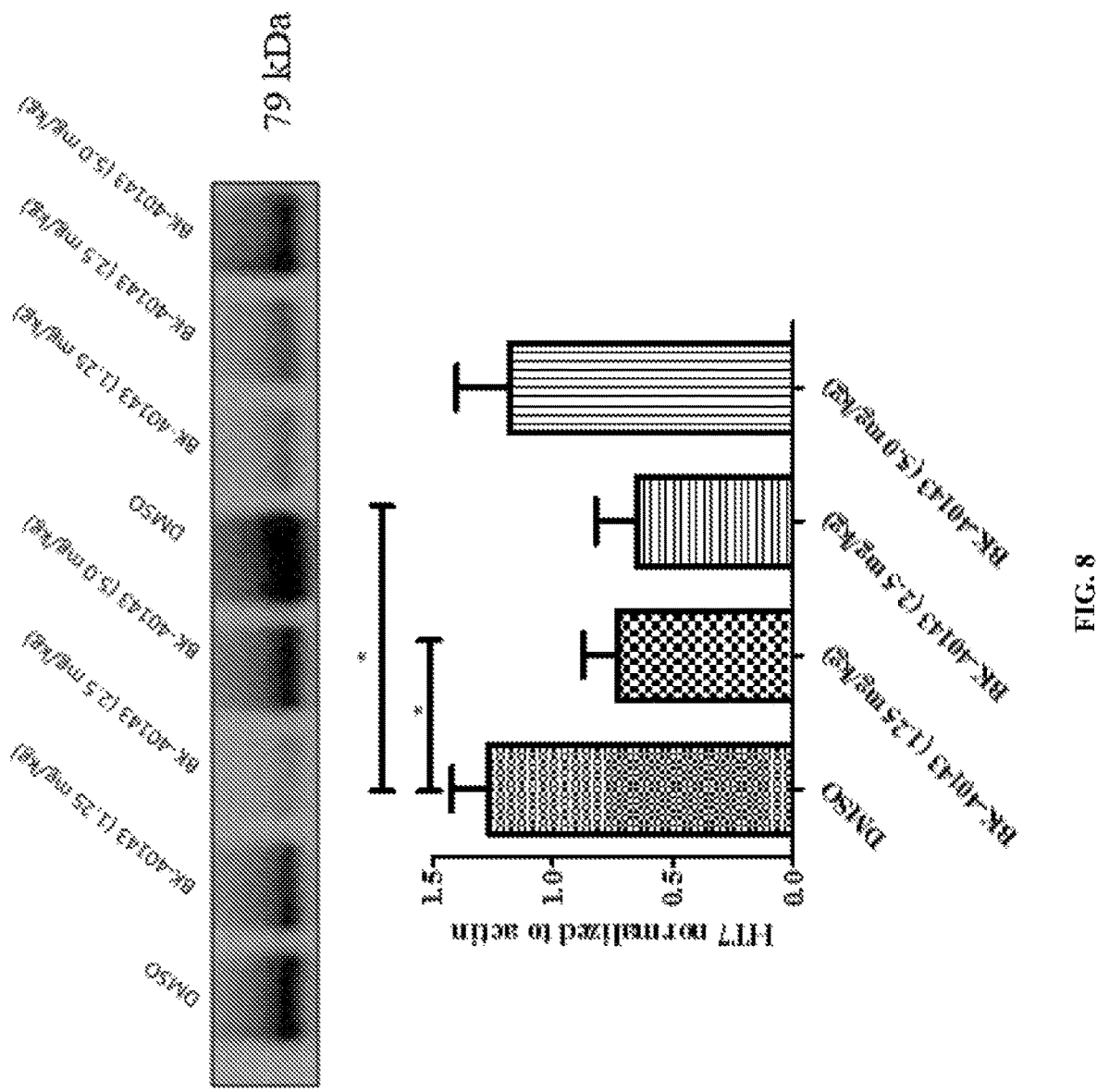
FIG. 8 shows that Tau (HT7) was significantly reduced in Tau transgenic mice after seven days of treatment with BK-41043, at 1.25 mg/kg and 2.5 mg/kg. Students t-test: unpaired, two-tailed, Welch's correction, *p<0.05, ***p<0.01, n=4

FIG. 8 shows that Tau (HT7) was significantly reduced in Tau transgenic mice after seven days of treatment with BK-41043, at 1.25 mg/kg and 2.5 mg/kg.

Figure 9:
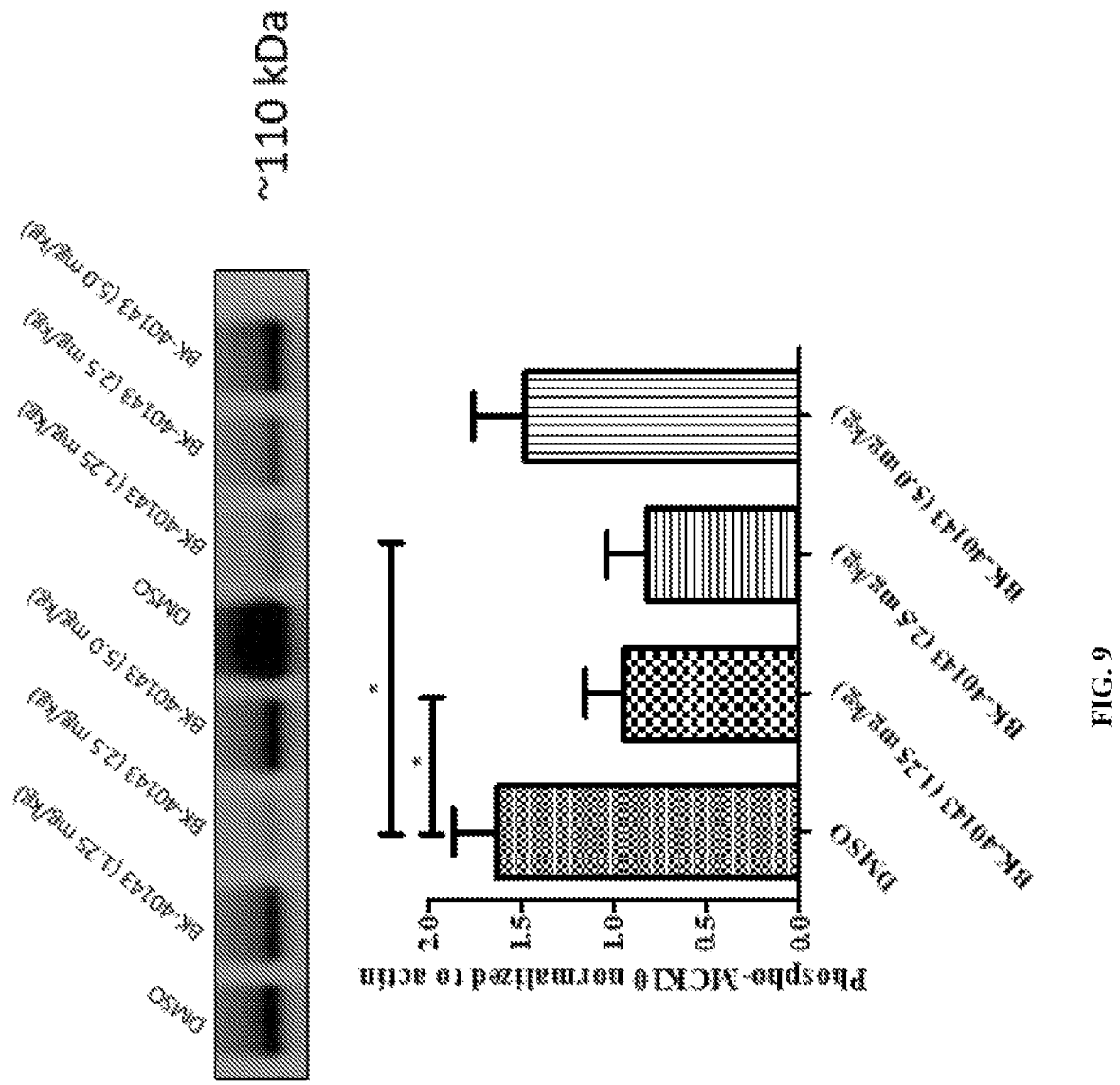
FIG. 9 shows that treatment with BK-40143 (1.25 mg/kg or 2.5 mg/kg) results in in vivo inhibition of DDR1, as measured by detection of phosphorylated (active) DDR1 (pMCK10). This data indicate that BK40143 potently inhibits DDR in vivo.

FIG. 9 shows that treatment with BK-40143 (1.25 mg/kg or 2.5 mg/kg) results in in vivo inhibition of DDR1, as measured by detection of phosphorylated DDR1 (pMCK10).

Figure 10:
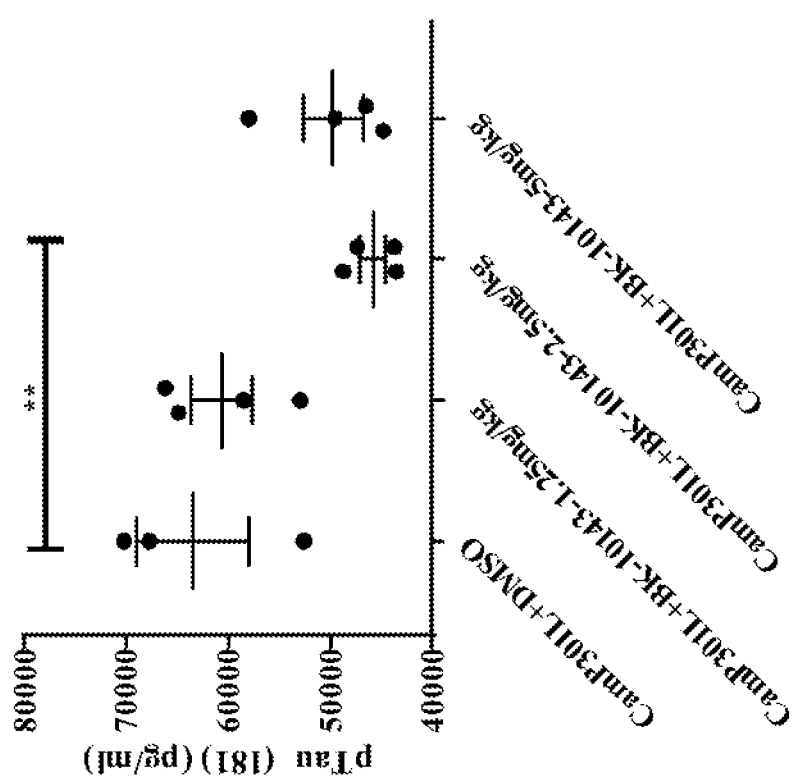
FIG. 10 shows that pTau (191) was reduced in CamP301 L mice after treatment with 2.5 mg/kg or 5 mg/kg BK-40143. Student's t-test: unpaired, Welch's correction, 1 tailed, *p>0.05, p=0.02, n=4.

FIG. 10 shows that pTau was reduced in CamP301L mice after treatment with 2.5 mg/kg or 5 mg/kg BK-40143.

As shown in FIG. 11, BK40196 reduced alpha-synuclein at high concentrations and BK40197 does not reduce alpha-synuclein. 1 mM and 100 uM of BK40196 significantly reduced the level of alpha-synuclein in transfected B35 cells (FIG. 11A). BK40197 does not display any ability to reduce alpha-synuclein levels in transfected B35 cells (FIG. 11B).

As shown in FIG. 12A, BK-40143 significantly decreased alpha-synuclein in A53T mice, compared to DMSO treated control A53T mice. C57BL/6J mice were used as controls and show no detectable (N.D.) human alpha-synuclein. FIG. 12B shows that BK-40143 insignificantly increases (about 30%) the overall level of dopamine, however BK-40143 did increase the level of the dopamine metabolite, homovanillic acid (HVA), in A53T mice indicating more dopamine turnover which could result in better dopamine neurotransmission. The immunoblots shown in FIGS. 12C and 12D for alpha-synuclein (ThermoFisher, MAI-12874) mirrored the 40% reduction in alpha-synuclein seen in the ELISA.

Figure 13:
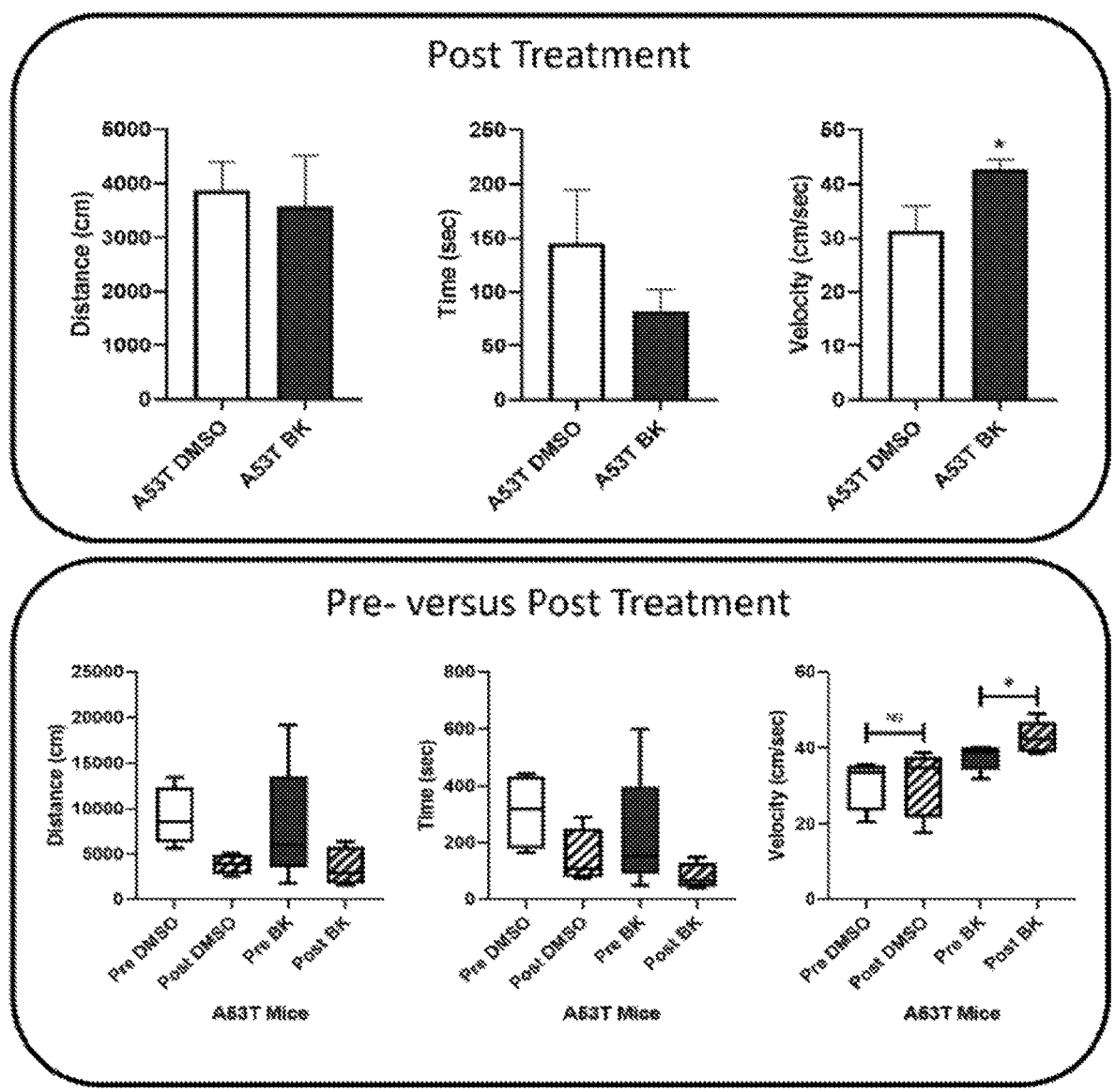
FIG. 13 shows that BK40143 improves velocity of locomotion in A53T mice, A53T mice were tested on the open field test for overall locomotor ability over a 60-minute trial. Although the mice did not show any difference in the total distance travelled or total time spent moving, the velocity of their movements significantly increased with BK40143 treatment.

Animal studies also showed that BK-40143 improved velocity of locomotion in A53T mice. A53T mice were tested on the open field test for overall locomotor ability over a 60-minute trial. Although the mice did not show any difference in the total distance travelled or total time spent moving, the velocity of their movements significantly increased with BK-40143 treatment (FIG. 13). This could be a reflection of better dopamine neurotransmission as indicated by the increased levels of HVA after BK (FIG. 12B).

Figure 14:
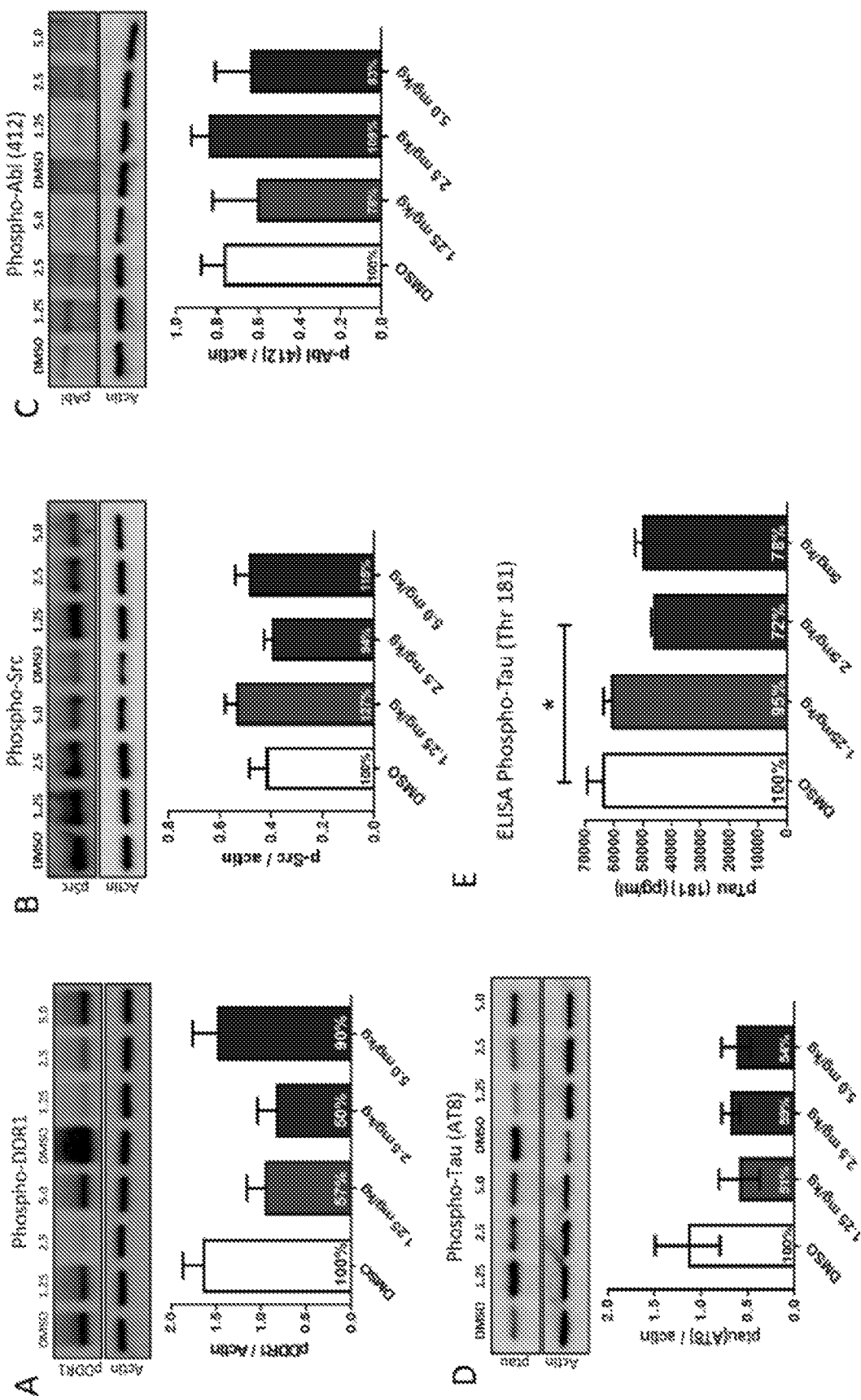
FIGS. 14A-E show that BK40143 selectively deactivates DDRs (about 50%) but not Src or Ab1 and reduces phosphorylated tan in the rTG4510 tauopathy mouse model. Male and female, 3-month-old rTG4530 mice were treated i.p. with 1.25 mg/kg, 2.5 mg/kg, or 5 mg/kg of BK40143 or DMSO for 7 consecutive days.

It was also shown that BK40143 selectively deactivates DDRs but not Src or Ab1 and reduces phosphorylated tau in the rTG4510 tauopathy mouse model. Male and female, 3-month-old rTG4530 mice were treated i.p. with 1.25 mg/kg, 2.5 mg/kg, or 5 mg/kg of BK40143 or DMSO for 7 consecutive days. FIG. 14A, an immunoblot probing for activated (phosphorylated) DDR1, demonstrates that 1.25 and 2.5 but not 5 mg/kg of BK40143 deactivated DDR. FIG. 148, an immunoblot probing for activated Src, demonstrates that BK-40143 does not engage this tyrosine kinase. FIG. 14C, an immunoblot probing for activated Ab1, demonstrates that BK-40143 does not engage this tyroskine kinase, i.e., DDR1. Upon probing for phosphorylated Tau (AT8), FIG. 14D shows that all three doses of BK-40143 reduced the levels of phosphorylated tan by 41-49% percent. As shown in FIG. 14E, an LISA for phosphorylated Tau (ATI 81) revealed that that 2.5 mg/kg of BK40143 significantly reduces phosphorylated Tau.

Figure 15:
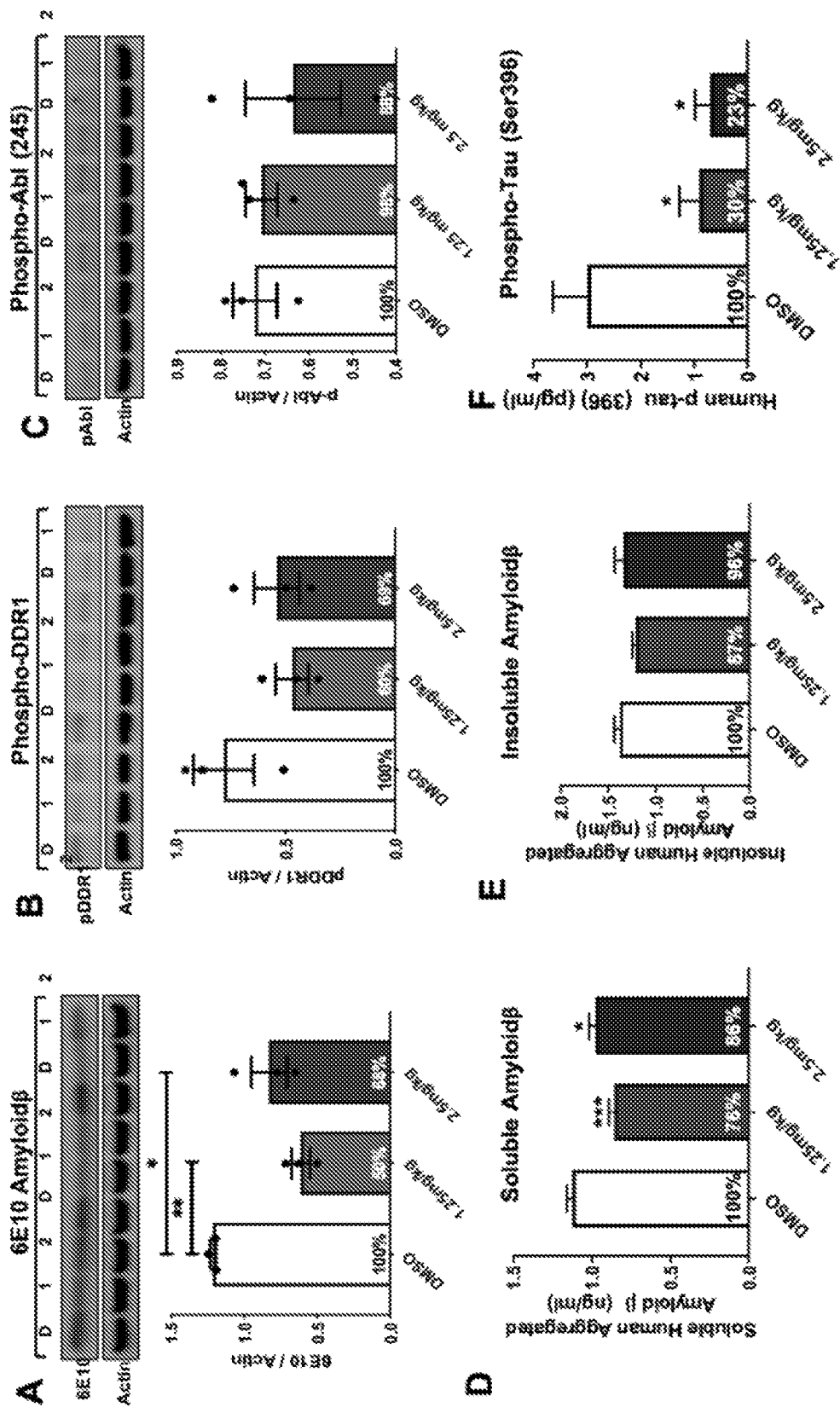
FIGS. 15A-F show that BK40143 significantly reduces amyloid, phosphorylated tau, and deactivates DDR1 in transgenic APP mice. Male and female, 7-month-old APP mice were treated i.p. with 1.25 and 2.5 mg/kg of BK40143 or DMSO for 21 consecutive days.

BK40143 also significantly reduced amyloid, phosphorylated tau, and deactivated DDR1. Male and female, 7-month-old APP mice were treated i.p. with 1.25 and 2.5 mg/kg of BK40143 or DMSO for 21 consecutive days. Immunoblotting for aggregating extracellular amyloid-beta (6E10) demonstrated that 1.25 and 2.5 mg/kg of BK40143 significantly reduced amyloid-beta plaques (FIG. 15A). Probing for phosphorylated DDR1 demonstrated that 1.25 and 2.5 mg/kg of BK40143 deactivated DDR1 by 40% and 31%, respectively (FIG. 15B). Probing for activated (phosphorylated Ab1 (245) demonstrated that BK40143 does not engage Ab1 (FIG. 15C). FIGS. 15D and 15E show that 1.25 and 2.5 mg/kg BK-40143 significantly reduced soluble human amyloid-beta via ELISA, but did not significantly reduce the insoluble amyloid-beta. Also shown is that 2.5 mg/kg of BK40143 significantly reduces human phosphorylated tau (Ser396) by over 80% (FIG. 15F).

Figure 16:
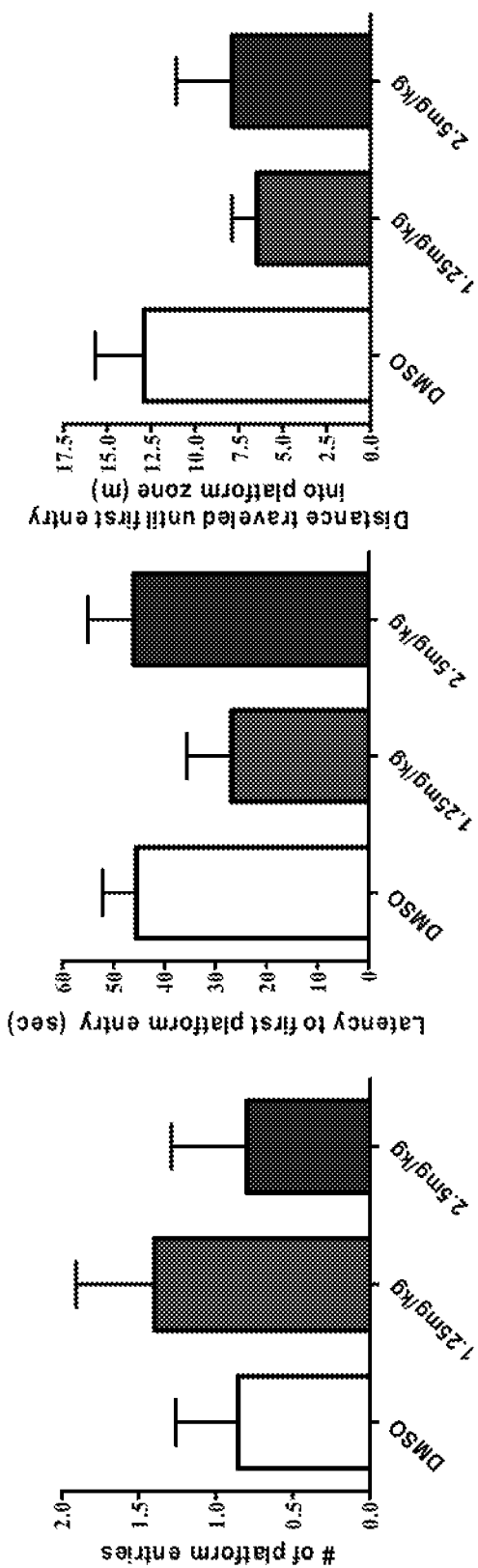
FIG. 16 shows that BK40143 could improve performance on Morris Water Maze test for cognition in APP mice. Measurements include the number of platform entries (left panel), the latency to the first entry (middle panel), and the distance travelled before their first entry (right panel) to the platform. Although there was no significant difference between groups, 1.25 mg/kg of BK showed a trend for increased performance with higher numbers of platform entries, and a lower latency to first entry and lower distance travelled before the first entry.

Also shown is that BK40143 could improve performance on Morris Water Maze test for cognition in APP mice. APP mice were tested on the morris water maze post-treatment for their ability to find a target platform. Measurements include the number of platform entries (FIG. 16, left panel), the latency to the first entry (FIG. 16, middle panel), and the distance travelled before their first entry to the platform (FIG. 16, right panel). Although there was no significant difference between groups, 1.25 mg/kg of BK-40143 shows a trend for increased performance with higher numbers of platform entries, and a lower latency to first entry and lower distance travelled before the first entry (FIG. 16).

Figure 17:
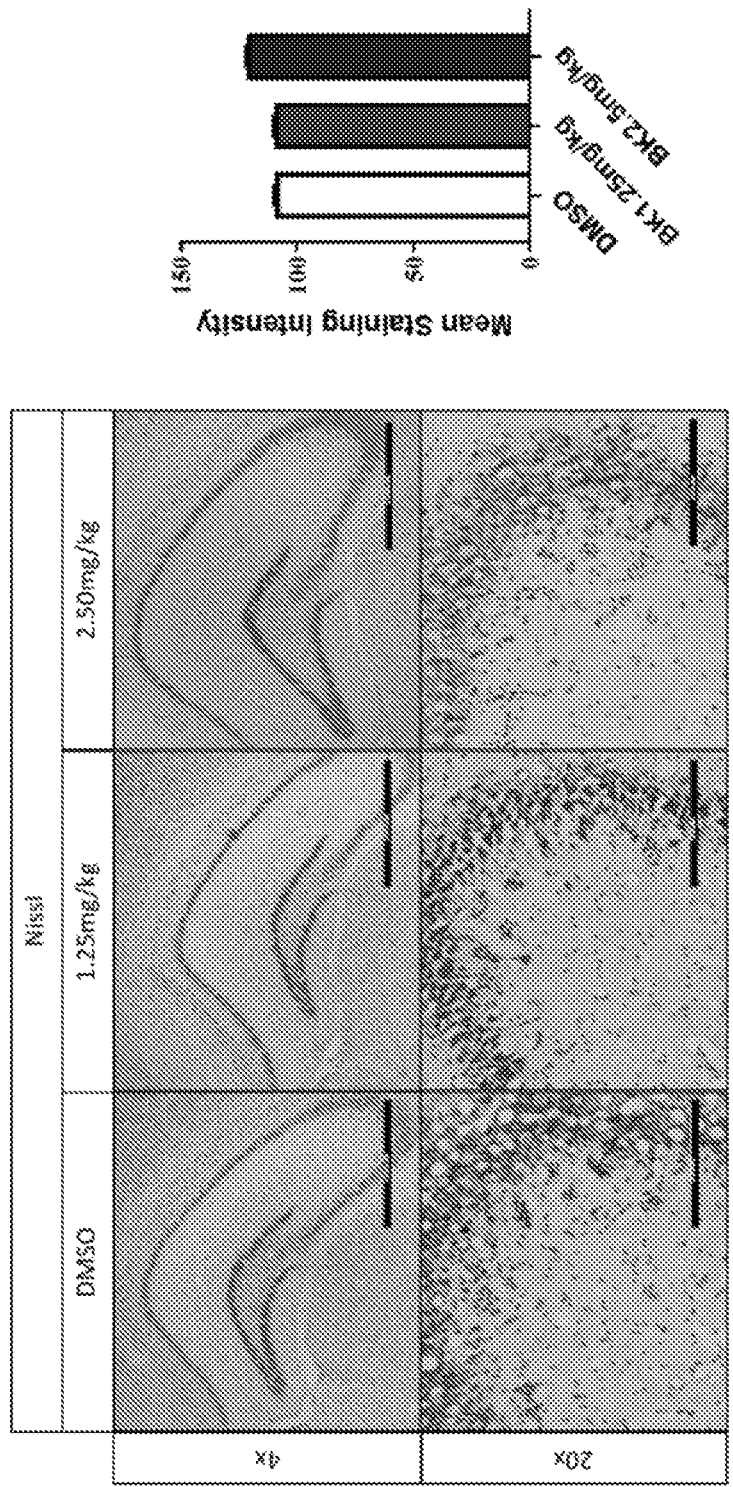
FIG. 17 shows that BK40143 does not cause cell death in the hippocampus of APP mice. Representative 20 um hippocampal sections were stained for niss1 substance (left panel). 4× and 20× images for DMSO, 1.25 mg/kg, and 2.5 mg/kg of BK40143 are shown (left panel). Mean staining intensity was quantified in imagej software as the total amount of niss1 staining in all 4× images (right panel).

Studies also showed that BK40143 does not cause cell death in the hippocampus of APP mice. Representative 20 um hippocampal sections were stained for Niss1 substance. 4× and 20× images for DMSO, 1.25 mg/kg, and 2.5 mg/kg of BK40143 are shown in FIG. 17 (left panel). Mean staining intensity was quantified in imagej software as the total amount of Niss1 staining in all 4× images (FIG. 17, right panel).

These data suggest that a compound of Formula I, for example, BK41043 or BK40197 can be used to treat or prevent a neurodegenerative disorder, a myodegenerative disorder or a lysosomal storage disorder.

What is claimed is:
1. A compound having the following formula:

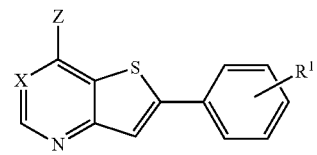

wherein
X is CH;
R$^1$ is —CH$_3$;
Z is heteroaryl, heterocyclyl, or NR$^3$R$^4$, wherein
R$^3$ and R$^4$ are independently H, C$_{1-3}$ alkyl, C$_{1-3}$ alkoxy, or unsubstituted phenyl, or a pharmaceutically acceptable salt thereof.

2. The compound of claim 1, wherein the compound does not comprise one or more halogen atoms.

3. The compound of claim 1, wherein the compound has the following formula:

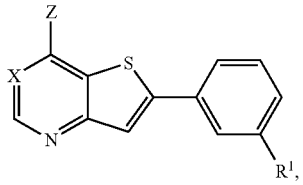

and wherein Z is heterocycl or wherein Z is morpholin-1-yl.

4. The compound of claim 1, wherein the compound has the following formula:

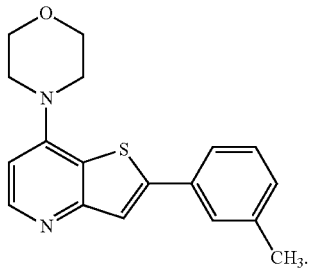 [SMILES: Cc1cccc(-c2cc3nccc(N4CCOCC4)c3s2)c1]

5. The compound of claim 1, wherein $R^3$ is H and $R^4$ is unsubstituted phenyl.

6. The compound of claim 1, wherein the compound has the following formula:

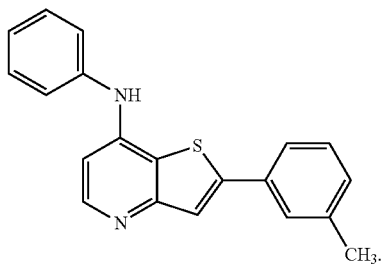 [SMILES: Cc1cccc(-c2cc3nccc(Nc4ccccc4)c3s2)c1]

7. A method of treating or preventing a neurodegenerative disease, a myodegenerative disease or prion disease in a subject, comprising administering to the subject with the neurodegenerative disease, the myodegenerative disease, or the prion disease or at risk for developing the neurodegenerative disease, the myodegenerative disease or the prion disease an effective amount of a compound having the following formula:

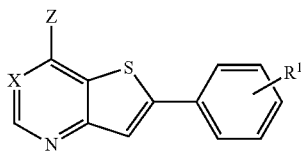

wherein,

X is CH;

$R^1$ is —$CH_3$; and

Z is heteroaryl, heterocyclyl, or $NR^3R^4$, wherein $R^3$ and $R^4$ are independently H, $C_{1-3}$ alkyl, $C_{1-3}$ alkoxy, or unsubstituted phenyl, or a pharmaceutically acceptable salt thereof.

8. The method of claim 7, wherein the compound has the following formula:

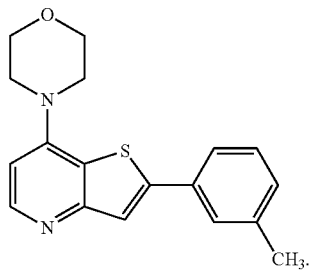 [SMILES: Cc1cccc(-c2cc3nccc(N4CCOCC4)c3s2)c1]

9. The method of claim 7, wherein the compound has the following formula:

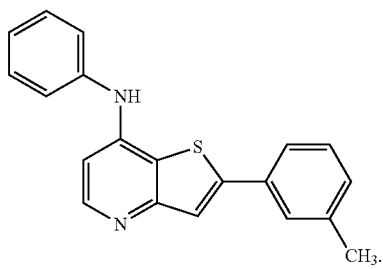 [SMILES: Cc1cccc(-c2cc3nccc(Nc4ccccc4)c3s2)c1]

10. The method of claim 7, wherein the neurodegenerative disease is selected from the group consisting of Amoytrophic Lateral Sclerosis, Alzheimer's Disease, Parkinson's Disease, Huntington's Disease, Mild Cognitive Impairment, an α-Synucleinopathy and a Taupathy.

11. The method of claim 7, wherein the compound is administered systemically or orally.

12. The method of claim 7, wherein the compound is in a pharmaceutical composition.

13. The method of claim 7, further comprising administering a second therapeutic agent to the subject.

14. The method of claim 13, wherein the second therapeutic agent is selected from the group consisting of levodopa, a dopamine agonist, an anticholinergic agent, a monoamine oxidase inhibitor, a COMT inhibitor, amantadine, donepezil, memantine, risperidone, rivastigmine, an NMDA antagonist, an acetylcholinesterase inhibitor, a cholinesterase inhibitor, riluzole, an anti-psychotic agent, an antidepressant, and tetrabenazine.

15. A method of inhibiting or preventing toxic protein aggregation in a neuron comprising contacting the neuron with an effective amount of a composition comprising a compound having the following formula:

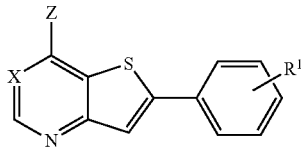

wherein,

X is CH;

R$^1$ is —CH$^3$; and

Z is heteroaryl, heterocyclyl, or NR$^3$R$^4$, wherein R$^3$ and R$^4$ are independently H, C$_{1-3}$ alkyl, C$_{1-3}$ alkoxy, or unsubstituted phenyl, or a pharmaceutically acceptable salt thereof.

16. The method of claim 15, wherein the compound has the following formula:

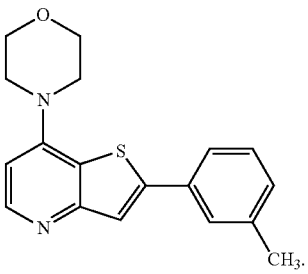 [SMILES: Cc1cccc(-c2cc3nccc(N4CCOCC4)c3s2)c1]

17. The method of claim 15, wherein the compound has the following formula:

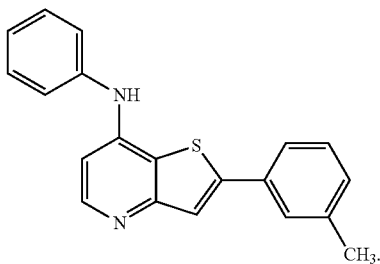 [SMILES: Cc1cccc(-c2cc3nccc(Nc4ccccc4)c3s2)c1]

18. The method of claim 15, wherein the protein is selected from the group consisting of an amyloidogenic protein, alpha-synuclein, tau and TDP-43.

19. The method of claim 15, wherein the contacting is performed in vitro or in vivo.

20. A method of treating or preventing a lysosomal storage disease (LSD) in a subject, comprising administering to the subject having the LSD an effective amount of a compound having the following formula:

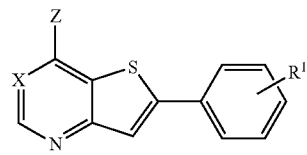

wherein,

X is CH;

R$^1$ is CH$^3$; and

Z is heteroaryl, heterocyclyl, or NR$^3$R$^4$, wherein R$^3$ and R$^4$ are independently H, C$_{1-3}$ alkyl, C$_{1-3}$ alkoxy, or unsubstituted phenyl, or a pharmaceutically acceptable salt thereof.

21. The method of claim 20, wherein the compound has the following formula:

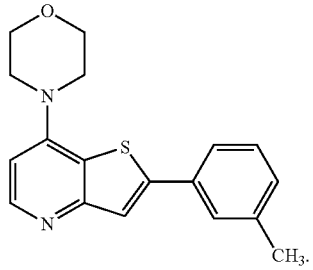 [SMILES: Cc1cccc(-c2cc3nccc(N4CCOCC4)c3s2)c1]

22. The method of claim 20, wherein the compound has the following formula:

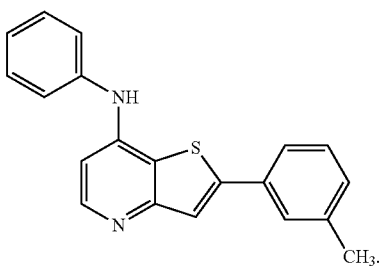 [SMILES: Cc1cccc(-c2cc3nccc(Nc4ccccc4)c3s2)c1]

23. The method of claim 20, wherein the subject is a pediatric subject.

24. The method of claim 20, wherein the effective amount of compound inhibits or prevents toxic substance aggregation in one or more cells of the subject.

25. The method of claim 24, wherein the one or more cells are brain cells, cells in one or more peripheral tissues of the subject, or a combination thereof.

26. The method of claim 25, wherein the brain cells are neurons and/or glial cells.

27. The method of claim 20, further comprising administering a second therapeutic agent or therapy to the subject.

28. The method of claim 27, wherein the second therapeutic agent or therapy is selected from the group consisting of: enzyme replacement therapy, gene therapy, a hematopoietic stem cell transplant and a small molecule.

* * * * *